(12) United States Patent
Aust et al.

(10) Patent No.: US 6,485,756 B1
(45) Date of Patent: Nov. 26, 2002

(54) STABLE, HOMOGENEOUS NATURAL PRODUCT EXTRACTS CONTAINING POLAR AND APOLAR FRACTIONS

(75) Inventors: Duncan T. Aust, Ridge; James M. Wilmott, Shoreham, both of NY (US)

(73) Assignee: Collaborative Technologies, Inc., Stony Brook, NY (US)

( * ) Notice: Subject to any disclaimer, the term of this patent is extended or adjusted under 35 U.S.C. 154(b) by 0 days.

(21) Appl. No.: 09/544,649

(22) Filed: Apr. 6, 2000

Related U.S. Application Data

(60) Provisional application No. 60/127,930, filed on Apr. 6, 1999.

(51) Int. Cl.$^7$ .................................................. A61K 35/78
(52) U.S. Cl. ..................... 424/725; 514/937; 424/769; 424/729; 424/745; 424/757; 424/764
(58) Field of Search ........................ 724/195.1; 424/725, 424/450, 401, 455, 745, 729, 769, 757, 764; 514/937

(56) References Cited

U.S. PATENT DOCUMENTS 5,230,916 A * 7/1993 Chang et al.
5,800,818 A * 9/1998 Pruguaud et al.
6,274,358 B1 * 8/2001 Holtz et al.

* cited by examiner

Primary Examiner—Christopher R. Tate
Assistant Examiner—Michele C. Flood
(74) Attorney, Agent, or Firm—Darby & Darby

(57) ABSTRACT

Disclosed are stable, homogeneous dispersions, comprising (a) from about 20 to 90% by weight of a first composition comprising (i) about 60–95% by weight of a first polar solvent, (ii) about 0–40% by weight of one or more second polar solvents, and (iii) water soluble components of a first natural product; and (b) from about 10 to 60% by weight of a second composition comprising: (i) one or more apolar solvents, and (ii) oil soluble organic components of a second natural product; and (c) from about 0.01 to 80% by weight of a non-surface active lipid phosphate or a surface active agent. Also disclosed are methods of forming the stable, homogeneous dispersions of the invention, comprising forming a first composition comprising water soluble components of a first natural product; forming a second composition comprising oil soluble organic components of a second natural product; mixing the compositions and subjecting the mixture to high pressure high shear processing to form a stable, homogeneous dispersion.

16 Claims, 13 Drawing Sheets

STABLE, HOMOGENEOUS NATURAL PRODUCT EXTRACTS CONTAINING POLAR AND APOLAR FRACTIONS

This application claims priority under 35 U.S.C. §119(e) of prior provisional application Ser. No. 60/127,930, filed Apr. 6, 1999.

FIELD OF THE INVENTION

This invention is directed to the field of compositions comprising natural product extracts for use in personal care products or pharmaceuticals.

BACKGROUND OF THE INVENTION

Natural products and natural product extracts are often used in cosmetic and pharmaceutical applications. Natural products, particularly botanically sourced natural products, have demonstrable beneficial properties on the skin and hair. Extracts of these natural products have demonstrated antimicrobial, antiseptic, anti-inflammatory, antioxidant, enzyme stimulation or inhibition, pigmentation enhancement or control, photoprotective and many other physiological benefits.

Typically, the solvent systems used to produce these extracts are polar in nature, and most typically are water or glycols or a combination thereof. These polar solvents enable the extraction of only a similarly polar material from the biomass of the natural product material. Similarly, apolar solvents have been used to remove the apolar fractions from the biomass of the natural product materials. There is currently no single universal solvent capable of only extracting both the desired polar and apolar fractions. As a result, typical natural product extracts only provide a portion of the physiologically or aesthetically beneficial components.

It has not been possible to date to combine an aqueous extract with a lipid or other apolar phase into a single system without the use of surface active agents and special processing conditions to form emulsions or dispersions. Surface active agents permit the mixing of a hydrophilic phase and a hydrophobic phase by lowering the surface tension between the two phases, thereby creating micellar structures which, when mixed with a suitable processing procedure, produce stable systems. However, these surface active agents may be irritating to users, and the processes used to prepare the emulsions or dispersion make them difficult to reproduce.

Since many bioreactive or aesthetic components of the natural product are located within the structure of the cell wall or other organelles within the cell, a suitable process is required to extract the desired components from the cell. Simple solvent extraction is usually insufficient to remove the protected material from the cell. The cell wall barrier must be perturbed or ruptured sufficiently to allow diffusion to occur into the extracting solvent. A method is therefore needed to rupture cell walls and membranes to maximize the removal of the physiologically active or aesthetically pleasing materials. Examples of such process conditions include the use of heat, high shear mixing, ultrasonic waves, microwaves, high pressure and prolonged polar or apolar dialysis.

It is preferred to combine the process described above with the use of separate polar and apolar solvents to remove the maximum amount of all of the materials of interest. It is further preferred to combine both the polar and apolar extracts into a single, homogeneous preparation without the use of surface active agents which can cause irritation.

OBJECTS OF THE INVENTION

It is therefore an object of the present invention to provide an improved method of obtaining a composition comprising both the hydrophobic and hydrophilic components of a natural product or blend of natural products.

It is another object of the present invention to provide a single composition having both oil soluble and water soluble components of a natural product extract, in order to take advantage of synergy which is often associated with the use of multiple components of a natural product.

It is another object of the present invention to provide a greater functional activity due to the presence of a full complement of polar and apolar materials with physiologically beneficial or aesthetically pleasing properties.

It is another object of the present invention to provide a composition having greater potency and stability of the desired components, in comparison to prior art compositions.

It is another object of the present invention to provide better delivery of the physiologically beneficial active agents to sites within the skin or hair, where the active agents are needed for activity.

It is another object of the present invention to provide ease of manufacture of a finished system containing the full complement of extracts, yielding cost savings and greater reproducibility with consistent quality standards.

It is another object of the present invention to provide a greater versatility to compositions of natural product extracts that can be achieved by preparing prior art homogeneous or heterogeneous complexes.

It is another object of the present invention to provide a composition useful for personal care, pharmaceutical or cosmetic applications, having low irritation due to the absence of surface-active agents that lower the surface tension between immiscible phases.

Applicants have discovered methods of forming stable, homogeneous compositions comprising both polar and apolar fractions of natural product extracts. The applicants have now discovered that aqueous or aqueous/glycolic extracts can be successfully mixed with apolar extracts (e.g. silicone extracts) using high pressure, high shear processing to produce a single, stable homogeneous system that contains the entire complement of polar and apolar fractions from a selected natural product.

SUMMARY OF THE INVENTION

The invention is directed to stable, homogeneous dispersions comprising a water-soluble natural product extract and an oil soluble natural product extract. In certain embodiments, the dispersion does not comprise a surface active agent.

In one embodiment, the invention is directed to stable, homogeneous dispersions comprising a first composition which contains one or more polar solvents and water (or polar solvent) soluble components of a first natural product; and a second composition comprising one or more apolar solvents and oil (or apolar solvent) soluble organic components of a second natural product. Optionally, the dispersion may also comprise from about 0.01 to 8% by weight of a non-surface active lipid phosphate or a surface active agent.

In preferred embodiments, the invention is directed to stable, homogeneous dispersions comprising
 (a) from about 20 to 90% by weight of a first composition comprising:
  (i) about 60–95% by weight of a first polar solvent;
  (ii) about 0–40% by weight of one or more second polar solvents; and
  (iii) water soluble components of a first natural product; and
 (b) from about 10 to 60% by weight of a second composition comprising:

(i) one or more apolar solvents; and
(ii) oil soluble organic components of a second natural product; and
(c) from about 0.01 to 8% by weight of a non-surface active lipid phosphate or a surface active agent.

In particular embodiments, the first polar solvent may be water and the second polar solvent is selected from the group consisting of water; a mono, di, tri or polyhydroxy alkyl derivative; a mono, di, tri or polyhalogenated alkyl derivative; a mono, di, tri or poly alkyl ether derivative; and a mono, di, tri or poly carboxyl alkyl derivative. The apolar solvent may be one or more of an oil (such as a vegetable oil); a mono, di, tri or polyalkyl ester or ether of a mono, di, tri or polyhydroxy compound; a saturated, unsaturated, linear, branched, or cyclic hydrocarbon; a saturated, unsaturated, linear or branched $C_8$ to $C_{30}$ fatty acid; a branched, linear, or cyclical silicone or silicone derivative; or a homopolymer or heteropolymer fluid formed by the polymerization of alkylene oxide monomers.

The dispersion may comprise components from any of the natural products which are known to contain physiological properties. Examplary natural products are mulberry, lavender, licorice root, arnica, eyebright and grape root. The invention contemplates the use of water and oil soluble components of natural products which may be obtained by any of the methods known to those skilled in the art.

The invention is also directed to methods of forming the dispersions of the invention. In one embodiment, the process includes the steps of obtaining a first natural product extract comprising a polar solvent and water based components of a natural product; obtaining a second natural product extract comprising an apolar solvent and oil soluble components of a natural product; combining the first and second extracts to form a composition; optionally adding about 0.01 to 8% by weight of a non-surface active lipid phosphate or a surface active agent; and subjecting said mixture to high pressure high shear processing to form a stable, homogeneous dispersion.

Preferred rates of high pressure, high shear processing are at a pressure of about 11,000 to about 27,000 psi, and at a shear rate which is sufficient to form a dispersion having an average particle size of from about 200 to about 1,000 nm.

DETAILED DESCRIPTION OF THE INVENTION

Figure 1:
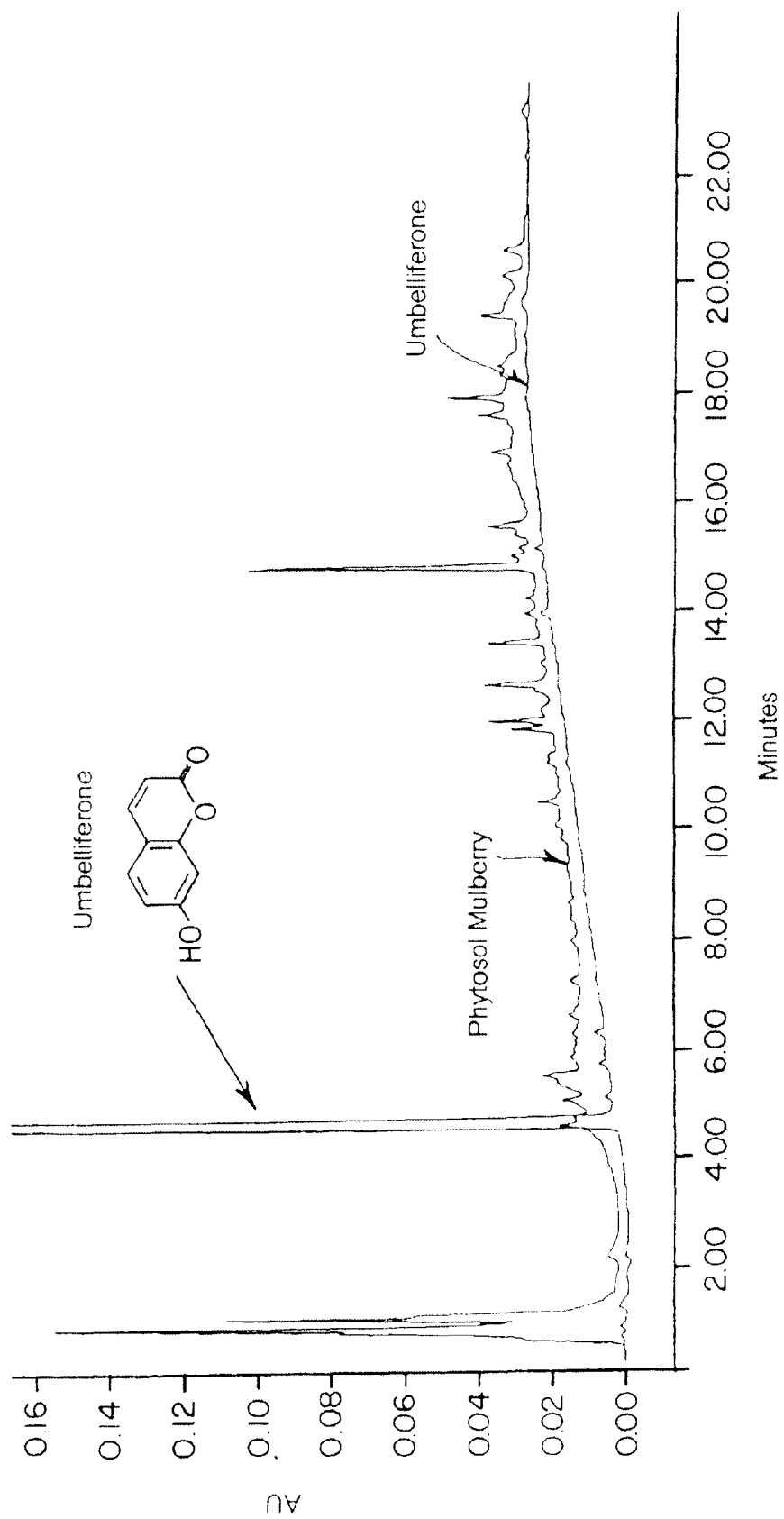
FIG. 1 is a chromatogram of a composition containing the polar solvent soluble components of mulberry.

All patents, applications, test methods and publications referenced in this specification are hereby incorporated by reference in their entirety. In case of conflict, the present description, including definitions, will prevail.

As used herein, the terms "water soluble" and "polar solvent soluble" are used interchangeably, and refer to the property of being soluble at approximate room temperature and one atmosphere pressure in water or another polar solvent commonly used in preparing cosmetic formulations, such as a glycol.

As used herein, the term "polar solvent soluble components" refers to the components of a natural product which may be extracted from the natural product by contacting the natural product with a polar solvent, for example water or glycol or mixtures thereof.

As used herein, the terms "oil soluble" and "apolar solvent soluble" are used interchangeably, and refer to the property of being soluble at approximate room temperature and one atmosphere pressure in an oil or other apolar solvent commonly used in preparing cosmetic formulations, such as silicone based solvents or oils or mixtures thereof.

As used herein, the term "organic oil soluble components" refers to the components of a natural product which may be extracted from the natural product by contacting the natural product with an apolar solvent, such as silicone or oils or mixtures thereof.

As used herein, the term "extracts" or "natural product extracts" are used interchangeably, and refer to the organic components of a natural product which can be obtained by contacting the natural product with a polar or apolar solvent.

As used herein the term "surface-active" or "surface-active agent" refers to a substance capable of reducing the surface tension of a liquid in which it is dissolved. A "non-surface active agent" is a substance which does not effectively reduce the surface tension of a liquid in which it is dissolved.

As used herein, the term "surfactant" refers to a surface-active substance.

As used herein, the term "surfactant-free dispersion" refers to a stable or dispersion that is produced without the use of surface-active ingredients or surfactants.

The present invention is directed in part to compositions containing natural product extracts which can be used in personal care and pharmaceutical formulations and products. In some embodiments, the invention is directed to a natural product extracts or combinations of natural product extracts containing hydrophilic and hydrophobic materials which are processed to produce a composition with physiologically beneficial and aesthetically pleasing properties. These natural products can be either animal or vegetable derived. In preferred embodiments, the invention is directed to compositions comprising natural product extracts from land-based or marine-derived botanicals.

In one embodiment, the compositions of this invention are dispersions which may comprise both polar solvent soluble components of a natural product and apolar solvent soluble components of a natural product. The polar solvent soluble components may be present in a composition also comprising one or more polar solvents, and the polar solvent soluble components may be present in a second composition, also comprising one or more apolar solvents.

The first composition used to form the dispersion may contain the organic polar solvent soluble components of a natural product. In preferred embodiments, the dispersion may comprise a first composition, which contains polar solvent soluble components of a natural product. The first composition may contain first and second polar solvents. The first polar solvent may be present in the amount of about 60 to 95% by weight of the first composition. The first composition may also comprise a second polar solvent, which may be present in the amount of about 0 to 40% by weight.

In preferred embodiments, the first polar solvent is water and the second polar solvent is a glycol, such as propylene glycol or ethylene glycol.

The first composition may be present in the amount of about 20 to 90% by weight of the dispersion, and is preferably present in the amount of 40 to 80 wgt %, more preferably 50 to 70 wgt %, most preferably 60 to 65 wgt %.

The dispersion also comprises the organic apolar solvent soluble components of a natural product, for example in the form of a second composition which contains apolar solvent soluble organic components of a natural product and an apolar solvent.

The second composition may be present in the amount of about 10 to 60% by weight of the dispersion, and is preferably present in the amount of 20 to 50 wgt %, more preferably 30 to 40 wgt %, and most preferably about 30 wgt %.

In certain embodiments, the natural product extracted in the first and second composition are the same. However, the invention also contemplates dispersions in which the natural product extracts present in the first and second compositions are obtained (or extracted) from different natural products. In addition, the invention contemplates dispersions in which either (or both) of the first and second compositions comprises extracts or components of more than one natural product.

In preferred embodiments, the dispersion is a surfactant free dispersion, and does not contain a surface active agent.

Phospholipids are one agent which may be used to achieve surfactant-free dispersions of the invention. Phospholipids in general are not soluble in water. In contrast, surface active materials reduce the surface tension of the liquid in which it is dissolved.

For example, when lecithin is refined and the concentrations of phosphatidyl choline increase, the surface tension of dispersions of the phospholipid in water increase. At concentrations of 50% phosphatidyl choline and higher, the surface tension exceeds the surface tension of water alone by a very considerable level. The conditions involved for the surface tension measurement are for a condensed, solid monolayer of phosphatidyl choline. The ability to achieve the monolayer is dependent on first processing the phosphatidyl choline above its phase transition temperature of 41° C., and then allowing the condensed monolayer to cool. This notion of phase transition associated with increased energy is important in consideration of phospholipids, and particularly phosphatidyl choline, as a means of achieving surfactant-free emulsions.

In particular embodiments, the dispersion may also comprise from 0.01% to 8% by weight (preferably 0.01 to 5% by weight) of one or more lipids. Examplary lipids include Phospholipon 80, 80H (American Lecithin) and Basis LP2OH (Ikeda Corp., Japan).

The components of the natural products may be obtained by various methods known to those of ordinary skill in the art. Polar solvent soluble components of a natural product may be obtained by contacting the natural product with a polar solvent to form a solution containing the polar solvent soluble components, optionally mixing the solution and optionally thereafter diluting the solution with another polar solvent. For example, a natural product can be contacted with water to form a solution containing water soluble components of the natural product, the solution may be mixed, and thereafter may be diluted with glycol. Alternatively, the natural product can be contacted with glycol to form a solution containing organic water soluble components of the natural product, the solution may be mixed, and thereafter diluting the solution with water. In still another method, the natural product can be contacted with both water and glycol to form a solution, and optionally mixed.

Polar solvent soluble (or water soluble) components of a natural product are obtained by contacting the natural product with a polar solvent, for example water, glycol, or mixtures thereof, to form a solution containing the polar solvent soluble components. If necessary, the solution may thereafter be mixed or stirred until the solution is clear.

Suitable polar solvents include water; glycols; mono, di, tri or polyhydroxy alkyl derivatives; mono, di, tri or polyhalogenated alkyl derivatives; mono, di, tri or polyalkyl ether derivatives; and mono, di, tri or polycarboxyl acid derivatives and mixtures thereof. Exemplary glycols include ethylene glycol, propylene glycol, 1,3-butylene glycol and glycerin.

Organic apolar solvent soluble (or oil soluble) components of a natural product are obtained by contacting the natural product with an apolar solvent, for example cyclomethicone, hydrogenated polyisobutene, or combinations thereof, to form a solution containing the organic polar solvent soluble components. If necessary, the solution may thereafter be mixed or stirred until the solution is clear.

Suitable apolar solvents include mono, di, tri or poly alkyl ester or ether of a di, tri, or polyhydroxy compound, such as ethylene glycol, propylene glycol, glycerin, sorbitol or other polyol compound. Examples of such esters and ethers include, but are not limited to, saturated and unsaturated, linear and branched vegetable oils, such as soybean oil, babassu oil, castor oil, cottonseed oil, chinese tallow oil, crambe oil, perilla oil, danish rapeseed oil, rice bran oil, palm oil, palm kernel oil, olive oil, linseed oil, coconut oil, sunflower oil, safflower oil, peanut oil and corn oil. Preferred saturated and unsaturated vegetable oils are those having fatty acid components with 6 to 24 carbon atoms. A more preferred vegetable oil is soybean oil.

Additional exemplary apolar solvents include compounds having the formula $C_nH_{(2n+2-m)}$ where n is an integer greater than or equal to 6 and m is 0 or an even integer no greater than n. Such compounds include, but are not limited to, saturated and unsaturated, linear, branched, and cyclic hydrocarbon chains. Preferred examples of such compounds include, but are not limited, mineral oil, petrolatum, permethyl fluids, polybutylenes, and polyisobutylenes.

Further apolar solvents contemplated for use in the invention have the formula

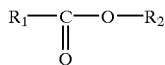

or the formula

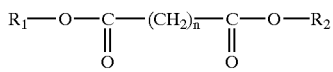

where $R_1$ is a saturated or unsaturated, linear, branched or cyclic $C_1$–$C_{24}$ alkyl; $R_2$ is hydrogen or a saturated or unsaturated, liner, branched or cyclic $C_1$–$C_{24}$ alkyl; and n is an integer from 0 to 20. Examples of such aesthetic modifying agents include, but are not limited to, isopropyl palmitate and diisopropyl adipate.

Yet another group of apolar solvents is silicone and silicone derivatives. Silicone may provide lubrication and/or shine to the composition. Preferably, the silicone is insoluble in water. Suitable water-insoluble silicone materials include, but are not limited to, polyalkylsiloxanes, polyarylsiloxanes, polyalkylarylsiloxanes, polysiloxane gums and polyethersiloxane copolymers. Examples of suitable silicone materials are disclosed in U.S. Pat. Nos. 4,788,006; 4,341,799; 4,152,416; 3,964,500; 3,208,911; 4,364,837 and 4,465,619, all of which are incorporated herein by reference.

Another suitable hydrophobic material which can be suspended in the composition has the formula

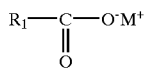

where $R_1$ is a saturated or unsaturated, linear, branched or cyclic alkyl having 2 to 24 carbon atoms; $M^{(+)}$ is $N^+R_2R_3R_4R_5$; $R_2$, $R_3$ and $R_4$ are hydrogen or a saturated or unsaturated, linear alkyl or hydroxyalkyl having from 1 to 10 carbon atoms; and $R_4$ is a saturated or unsaturated, linear, branched or cyclic alkyl or substituted alkyl having 2 to 24 carbon atoms. An example of such a material is lauramine oleate.

Another apolar solvent is a polymer formed by polymerization of alkylene oxide monomers of the formula

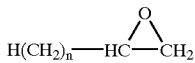

where n is from about 2 to about 24. The polymer may be either a homogenous polymer or a copolymer. Examples of such homogenous polymers include, but are not limited to, polypropylene oxide and polybutylene oxide. Generally, the molecular weight of these polymers ranges from about 100 to about 10,000 daltons. Additionally, these polymers may be reacted with mono or polyhydroxyalkyl alcohol, such as UCON fluids from the Union Carbide Chemical Company, or with a saturated or unsaturated, linear, branched or cyclic $C_1$–$C_{24}$ alkyl.

Suitable apolar solvents include oils (both natural and synthetic), including hydrogenated oils. Exemplary oils include vegetable oil, soybean oil, babasu oil, castor oil, cottonseed oil, grapeseed oil, rice bran oil, canola oil, palm oil, palm kernel oil, olive oil, linseed oil, coconut oil, sunflower oil, safflower oil, peanut oil, corn oil, mineral oil and petrolatum. Other apolar solvents contemplated for use in the invention include hydrogenated polyisobutene, permethyl fluids, polyisobutene, polybutene, polypropylene oxide, polybutylene oxide, isopropyl palmitate, disopropyl adipate or mixtures thereof.

Exemplary silicone and silicone derivatives include branched or linear cyclical silicone or silicone derivatives, cyclomethicone, dimethicone polysiloxane, dimethicinol, polysiloxanes, polysiloxane copolymers, polyalkyl aryl silanes, polyaryl siloxanes, polyalkyl siloxanes, polyalkyl aryl silanes, polysiloxane copolymers, low viscosity dimethicone, phenyl trimethicone (Dow Corning), silicone fluid DC 345 (Dow Corning), polysynlane (NOF Corp.).

Still more suitable apolar solvents include mono, di, tri or polyalkyl esters or ethers or a mono, di, tri or polyhydroxy compound; saturated or unsaturated, linear or branched $C_8$–$C_{30}$ fatty acids; and homopolymer or heteropolymer fluids formed by the polymerization of alkylene oxide monomers.

The dispersions of the invention may be produced by mixing a water soluble natural product extract and an oil soluble natural product extract, using high pressure/high shear conditions to produce a homogeneous, fluid dispersion which is stable for a commercially relevant period of time, e.g. between about 180 to 720 days when stored at approximate room temperature, in a commercial package. The preferred pressure for preparation of this dispersion is between about 11,000 to about 27,000 psi, more preferably 11,000 to about 21,000 psi, most preferably between about 11,000 and 16,000 psi. The composition may be produced with a shear that creates average particle size of between about 100 to about 1,000 nm, more preferably between about 100–500 nm.

The invention is also directed in part to processes for efficiently rupturing the cell wall or lipid bilayer membrane of individual cells or subcellular organelles of the natural product to maximize the removal of the cellular components.

In certain embodiments, composition of the invention may comprise non-surface active lipid phosphate phospholipids, preservatives such as Germazide™ MPB, and nonionic detergents such as polyoxethylene ethers. The dispersion may also comprise polyethylene glycol and butylene glycol to improve the freeze thaw stability of the preparations.

Exemplary non-ionic detergents include polyoxylated ethers such as Brij detergents, available from Sigma Aldrich Chemical Co.

Suitable natural products contemplated for use in the invention include any of the natural products which are know in the art to contain components having physiological attributes. Exemplary natural products include mulberry (*morus alba*), lavender (*lavandula angustifolia*), licorice root (*glycyrrhiza glabra*), arnica (*arnica montana*), eyebright (*euphrasia officinalisa*), grape root (*mahonia aquifolum*), green tea leaves (*camelia sinesis*), rosemary powder, echinacea herb powder, evening primrose flowers, sea parsley powder (*palmaria palmata*), calendula leaves and tea tree leaves.

Recent research has shown that mulberry (*morus alba*) and licorice (*glycyrrhiza glabra*) root extracts act as tyrosinase inhibitors. Chemical analysis has shown that the plant contains a number of interesting biochemicals, in particular oxyresveratrol, umbelliferone, kowano-A, kowano-B, kowano-C, kowano-F, kowano-G, kowano-H, chalcomoracin, cyclomorusin, cyclomulberrin, cyclomulberrochromene moracenin-D, morusin, mulberranol, mulberrochromene, mulberrofuran-B, oxydihydromorusin, sitosterol and sitosterol-alpha-glucoside. The chemical or chemical(s) responsible for enzyme inhibition has not been unequivocally identified however researchers have shown that oxyresveratrol is a very potent tyrosinase inhibitor (Shin et al., *Oxyresveratrol as the Potent inhibitor on Dopa Oxidase Activity of a Mushroom Tyrosinase*, BBRC, 1998, vol. 243, pp 801–803).

Licorice root extract is used traditionally in balms for its powerful anti-inflammatory, anti-allergic and anti toxin properties. Recently, researchers have discovered that licorice root extract inhibits enzyme activities, especially tyrosinase and 11-beta-hydroxysteroid dehydrogenase and as a result it causes skin whitening and potentates the action of hydrocortisone. It is therefore of great interest to the pharmaceutical and cosmetic industries.

The major component of licorice root, glycyrrhizic acid, is important to the food industry. It is 50 times sweeter than sucrose (A. Chevallier, *The Encyclopedia of Medical Plants* p 99, 1996) making it a very useful food ingredient. Other active components of Licorice include the triterpine glycosides, glycyrrhizin, flavonoids, isoflanonoids, kumatakenin; licoricone, glabrol, glabrone, glyzarin, licoisoflavones A and B, glycyrol, formononetin, liquiritigenin, liquiritin, neoliguiritin, rhamnoliquiritin, glyzaglabin, 7-hydroxy-2-methylisoflavone, 4,7-dihydroxyflavone, glabranine, chalcones, coumarins, triterpenoids, sterols (including betasitosterol, stigmasterol), amino acids, gums, wax and volatile oil.

Lavender is associated with youthfulness. It is carminative, antiseptic and soothing. It is known amongst herbalists as a holistic relaxant or as "the balancing" herb. Lavender extracts have been analyzed and the major components, linalool and linalyl acetate, are just two among of the hundreds of different active compounds identified. Other significant components include triterpenes (e.g. ursolic), flavonoids (e.g. luteolin) and coumarins (A. Y. Leung et al., *Encyclopedia of Common Ingredients Used in Foods and Cosmetics*, 1996, pp 339–342). The ursolic acid and other components are known to be anti-inflammatory. The cosmeceutical benefits claimed for ursolic acid include restoration of overall health and functionality of photoaged skin, in addition to facilitation of tissue repair. Ursolic acid is a potent elastase inhibitor (Q. Ying et al., "Inhibition of Human Leukocyte Elastase by Ursolic Acid; Evidence for a Hydrophobic Binding Site for Pentacyclic Triterpenes, 1991, *Biochem. J.* 277, 521–526). Skin is a very dynamic tissue with degradation taking place along side repair and renewal. Compositions containing lavender extract improve skin integrity by slowing elastin degradation with respect to natural ongoing synthesis.

The mechanism by which lavender extracts 'relax' and reduce muscle tension has been studied in depth. M. Lis-Balchin et al., "Studies on the Mode of Action of the Essential Oil of Lavender (*Lavender Angustifolia*)", *Phytother. Res.*, 1999, 13(6), 540–542), showed that muscle tension is reduced through a postsynaptic action and not via an atropine-like mechanism and that the action of linalool reflected that of the whole lavender oil. (H. M. Kim et al., "Lavender Oil Inhibits Immediate Type Allergic Reaction in Mice and Rats," *J Pharm Pharmacol,* 1999, 51(2), 221–226, were more interested in lavender's 'soothing' properties. They studied the effects of lavender oil on mast cell-mediated allergic reactions in mice and rats and showed that the components of lavender oil inhibit immediate-type allergic reactions by inhibition of mast cell degranulation in vivo and in vitro. Other researchers have shown that when lavender is applied topically it stimulates the local circulation (Chevallier, 1996).

Evening Primrose (*oenothera biennis*) is a valuable source of γ-Linolenic Acid (GLA) and other special fatty acids that are essential for hormone function, energy flow, cell division, immune responses and many other aspects of metabolism. These critical fatty acids are used to make powerful tissue-specific compounds called eicosanoids.

GLA is effective at very low concentrations (M. S. Manku et al., Fatty acids in plasma and red cell membranes in normal humans, *Lipids,* 1983, 18(2);906). Doses of 1.4 g/d have resulted in clinically important reduction of the symptoms of rheumatoid arthritis (L. J. Leventhal et al., "Treatment of Rheumatoid Arthritis with a Gammalinolenic Acid," *Ann Int Med,* 1993,119(9); 867–73). 1–3 g/d is normally recommended for dietary supplements. When tiny amounts of GLA are applied to dry skin the skin soon shows signs of improvement. This is not surprising since one of the early signs of an individual being deficient in GLA is dry skin. Topical GLA application has been shown to promote the healthy growth of skin, hair, and nails and GLA has been used to successfully treat skin conditions such as atopic eczema. As well as being good for skin disorders, GLA is reported to be good for arthritis and autoimmune problems. (Leung et al., 1996, L. Galland, Increased Requirements for Essemtial Fatty Acids in Atopic Individuals; Review with Clinical Descriptions, 1999).

Individuals with normal metabolism can synthesize GLA from the essential fatty acid linoleic acid. The synthesis is controlled by the enzyme δ-6-desaturase. Interestingly, GLA corrects most of the biological effects of zinc deficiency (Y. S. Huang et al., "Moot Biological Effects of Line Deficiency Corrected by g-Linoleic Acid (18:3 omega-6) but not Atherosclerosis, by Linoleic Acid (18:2 omega-6), 1982, 41:193–207) indicating that δ-6-desaturase enzyme has a requirement for zinc that is a first-order essential function of zinc. GLA therefore, although not technically a vitamin, is an essential requirement for a significant number of individuals. Especially those whose δ-6-desaturase enzyme is blocked or its activity reduced. Interestingly, the ability to synthesize GLA is affected by factors such as the menstrual cycle and diet. GLA synthesis is reduced in diabetics or in individuals who fast or consume excessive amounts of carbohydrate (Leung et al., 1996). GLA levels also decrease with aging.

GLA can therefore be thought of in similar terms as a vitamin or an essential fatty acid. Moreover, GLA is being extensively studied and has been shown to be effective in killing cancer cells.

Eyebright is a plant that has been associated with eye care for generations. Eyebright infusions are mildly astringent but gentle enough to use on eyes. They are stimulating and have antioxidant and anti-inflammatory properties. The plant is recommended both historically and in modern literature for treating eye inflammations, particularly for conjunctivitis. Eyebright infusions bring rapid relief of redness, swelling and are very good at healing recent eye injuries. They are often recommended where there is a risk of developing serpiginous corneal ulcers (Leung et al., 1996).

Eyebright proves to be most effective when the whole plant is used. The plant is chopped up and applied as a compress (Chevallier, 1996). The active biochemicals present in Eyebright plant include the following: Iridoid glycosides, aucubin, catapol and erostoside, eukovoside, geniposide and luproside, gallotanins, caffeic acid and ferulic acids. The volatile oil contains trace amounts of the essential oils as well as beta-sitosterol, oleic acid, palmitic acid and stearic acid. Eyebright also contains miscellaneous unidentified alkaloid, amino acids, flavonoids and tannins.

In addition to the water soluble and oil soluble components of natural product extracts, in some embodiments the compositions of the invention may include various bioactive ingredients or cosmeceuticals, including antioxidants, skin whitening agents, elastase inhibitors, vitamins and active agents having anti-inflammatory, antiseptic, or soothing properties. The composition of the invention may be used in connection with the treatment of skin disorders, including eczema, psoriasis, acne, photoaging, dermatitis, would healing and dry skin.

In order to further illustrate the present invention, the experiments described in the following examples were conducted. It should be understood that the invention is not limited to the specific examples or the details described therein. The results obtained from the experiments described in the examples are shown in the accompanying figures and tables.

Exemplary Embodiments of the Invention

Natural product extracts (both oil soluble and water soluble extracts) and natural product extract compositions containing both oil soluble and water soluble components were formed according to Examples 1 to 26, as shown in Tables 1 to 3 below.

TABLE 1

| Silicone Extracts | Weight % of Oil Soluble Extracts | | | | | |
|---|---|---|---|---|---|---|
| | 1 | 2 | 3 | 4 | 5 | 6 |
| Mulberry, (*Morus alba*) dust-powder grade (China Products) | 2.5 | | | | | |
| Lavender, (*Lavandula angustifolia*) fine chopped plant grade (Aphrodisia) | | 2.5 | | | | |
| Licorice root, (*glycyrrhiza glabra*) powder grade (Lotus) | | | 2.5 | | | |
| Arnica (*Arnica montana*), herb powder (San Francisco Herb) | | | | 2.5 | | |
| Eyebright, (*euphrasia officinalisa*) fine chopped plant grade (Aphrodisia) | | | | | 2.5 | |
| Grape root, (*mahonia aquifolium*) coarse chopped grade (Aphrodisia) | | | | | | 2.5 |
| Silicone fluid DC 345 (Dow Corning) | 97.5 | 97.5 | 97.5 | 97.5 | 97.5 | 97.5 |

Method: Mix for 16 hrs and filter through Whatman #1 paper

| Silicone Extracts | 1a | 2a | 3a | 4a | 5a | 6a |
|---|---|---|---|---|---|---|
| Green tea (*Camelia Sinesis*) (China Products) | 2.5 | | | | 2.5 | |
| Rosemary powder (Aphrodisia) | | 2.5 | | | | |
| Calendula leaves | | | 2.5 | | | |
| Echinacea herb powder (San Francisco herb) | | | | 2.5 | | |
| Mulberry, (*Morus alba*) dust-powder grade (China Products) | | | | | | 2.5 |
| 0.65 cst silicone fluid DC200 (Dow Corning) | | | | | | 97.5 |
| Polysynlane (NOF Corp.) | | | | | 97.5 | |
| Phenyl Trimethicone (Dow Corning) | | | | 97.5 | | |
| Silicone fluid DC 345 (Dow Corning) | 97.5 | 97.5 | 97.5 | | | |

Method: Mix for 16 hrs and filter through Whatman #1 paper

TABLE 2

| Glycol Extracts | Extracts Composition - (Parts Per) | | | | | | | |
|---|---|---|---|---|---|---|---|---|
| | 7 | 8 | 9 | 10 | 11 | 12 | 13 | 14 |
| Mulberry, (*Morus alba*) dust-powder grade (China Products) | 1 | | | | | | | |
| Lavender, (*Lavandula angustifolia*) fine chopped plant grade (Aphrodisia) | | 1 | | | | | | |
| Licorice root, (*glycyrrhiza glabra*) powder grade (Lotus) | | | 1 | | | | | |
| Arnica (*Arnica montana*), herb powder (San Francisco Herb) | | | | 1 | | | | |
| Eyebright, (*euphrasia officinalisa*) fine chopped plant grade (Aphrodisia) | | | | | 1 | | | |
| Grape root, (*mahonia aquifolium*) coarse chopped grade (Aphrodisia) | | | | | | 1 | | |
| Tea Tree Leaves | | | | | | | 1 | |
| Evening Primrose Flowers | | | | | | | | 1 |
| Water | 125 | 125 | 125 | 125 | 125 | 125 | 125 | 125 |
| Propylene glycol (Kramer) | 10 | 10 | 10 | 10 | 10 | 10 | 4.5 | 4.5 |

Method: Mix botanical and propylene glycol for 5 hrs at room temperature and filter through Whatman #1 paper, then add the water at the above ratio and mix to produce the final extract as defined herein and preserve with an appropriate concentration of Germazide™.

| Glycol Extracts | 7a | 8a | 9a | 10a |
|---|---|---|---|---|
| Sea Parley (*Palmaria Palmata*) powder | 1 | | | |
| Gree Tea (*Camelia sinesis*) Leaves | | 1 | | |
| Rosemary Powder | | | 1 | |
| Calendula Leaves | | | | 1 |
| Glycerin | | 3.5 | 3.5 | 3.5 |
| Water | | 5.5 | 5.5 | 5.5 |
| 1-3,Butylene Glycol (Kramer) | 9 | | | |

Method: Mix botanical with polar solvent for 3 hrs at 40° C. and filter through Whatman #1 paper. An appropriate concentration of Germazide™ was then added.

TABLE 3

Compositions Comprising Both Oil Soluble and Water Soluble Extracts

| 15 | | 16 | | 17 | |
|---|---|---|---|---|---|
| (Mulberry) | Wt. % | (Lavender) | Wt. % | (Licorice) | Wt. % |
| Example 1 | 30 | Example 2 | 30 | Example 3 | 30 |
| Example 7 | 65 | Example 8 | 65 | Example 9 | 65 |
| Additive Lipid & Preservative | qs | Additive Lipid & Preservative | qs | Additive Lipid & Preservative | qs |

| 18 | | 19 | | 20 | |
|---|---|---|---|---|---|
| (Arnica) | Wt. % | (Eyebright) | Wt. % | (Grape Root) | Wt. % |
| Example 4 | 30 | Example 5 | 30 | Example 16 | 30 |
| Example 10 | 65 | Example 11 | 65 | Example 12 | 65 |
| Additive Lipid & Preservative | qs | Additive Lipid & Preservative | qs | Additive Lipid & Preservative | qs |

| 21 | | 22 | | 23 | |
|---|---|---|---|---|---|
| (Arnica) | Wt. % | (Eyebright) | Wt. % | (Grape Root) | Wt. % |
| Example 4 | 30 | Example 5 | 30 | Example 6 | 30 |
| Example 10 | 65 | Example 11 | 65 | Example 12 | 65 |
| Additive Lipid & Perservative | qs | Additive Lipid & Perservative | qs | Additive Lipid & Perservative | qs |

| 24 | | 25 | | 26 | |
|---|---|---|---|---|---|
| | Wt. % | | Wt. % | | Wt. % |
| Tea Tree Oil | 30 | Evening Primrose Oil | 30 | Evening Primrose Oil | 30 |
| Example 13 | 50 | Example 14 | 30 | Example 14 | 66.5 |
| Additive Lipid & Perservative | qs | Additive Lipid & Perservative | qs | Additive Lipid & Perservative | qs |

| 27 | | 28 | | 29 | |
|---|---|---|---|---|---|
| (Green Tea) | Wt. % | (Ros. Pwdr) | Wt. % | (Calendula) | Wt. % |
| Example 1a | 30 | Example 2a | 30 | Example 3a | 30 |
| Example 8a | 67.5 | Example 9a | 67.5 | Example 10a | 67.5 |
| Additive Lipid & Perservative | qs | Additive Lipid & Perservative | qs | Additive Lipid & Perservative | qs |

The term "qs" means a quantity to sufficient to constitute the remaining weight percent of the composition.

The additive lipid and preservative used in each of Examples 15–29 contains 2.35 wt. % phospholipid, 1.6 wt. % Germazide™ MPB , and qs with water.

Examples 15–29 were formed by mixing the contents of the composition, making the contents homogenous by using a Silverson high shear mixer. The composition is then processed through a M110 microfluidizer, manufactured by Microfluidics, Inc. of Massachusetts, at approximately 17,000 psi.

Mulberry Extract

In Example 1 (Table 1), a hydrophobic solution comprising the organic oil soluble materials in mulberry root was prepared by contacting mulberry with a silicone oil and mixing. The resulting composition was mixed and filtered to clarity. The Mulberry silicone extract was examined by HPLC (see FIG. 1) to ensure complete extraction.

In Example 7, the polar solvent soluble materials were derived from Mulberry. The Mulberry powder extract was obtained by contacting with propylene glycol and constant stirring for 5 hours at room temperature. The resulting composition was diluted with water and Germazide™ MPB was added.

Figure 2:
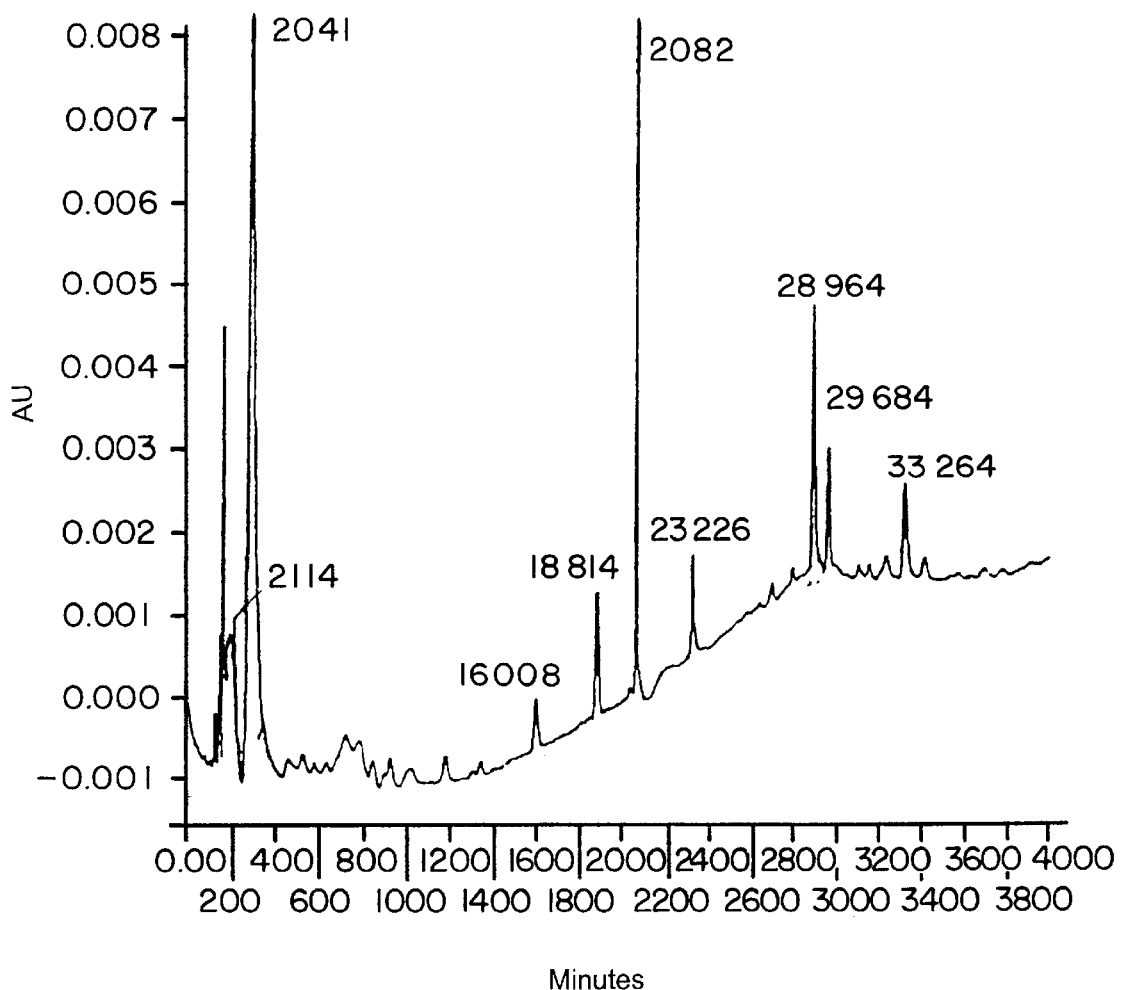
FIG. 2 is a chromatogram of a composition containing the apolar solvent soluble components of mulberry.

The HPLC traces for both the polar solvent soluble and apolar solvent soluble mulberry extracts are shown in FIGS. 1 and 2. It is clear that their overall composition is very different. The chromatogram of the apolar soluble material extracted from mulberry root (FIG. 2) is very different from the materials found in the chromatogram of the polar solvent soluble components (FIG. 1).

The two phases were mixed together along with phospholipid in a high shear mixer and then combined using high pressure, high shear processing to produce the dispersion of Example 15, containing both the polar and apolar solvent soluble organic components of mulberry.

Figure 3:
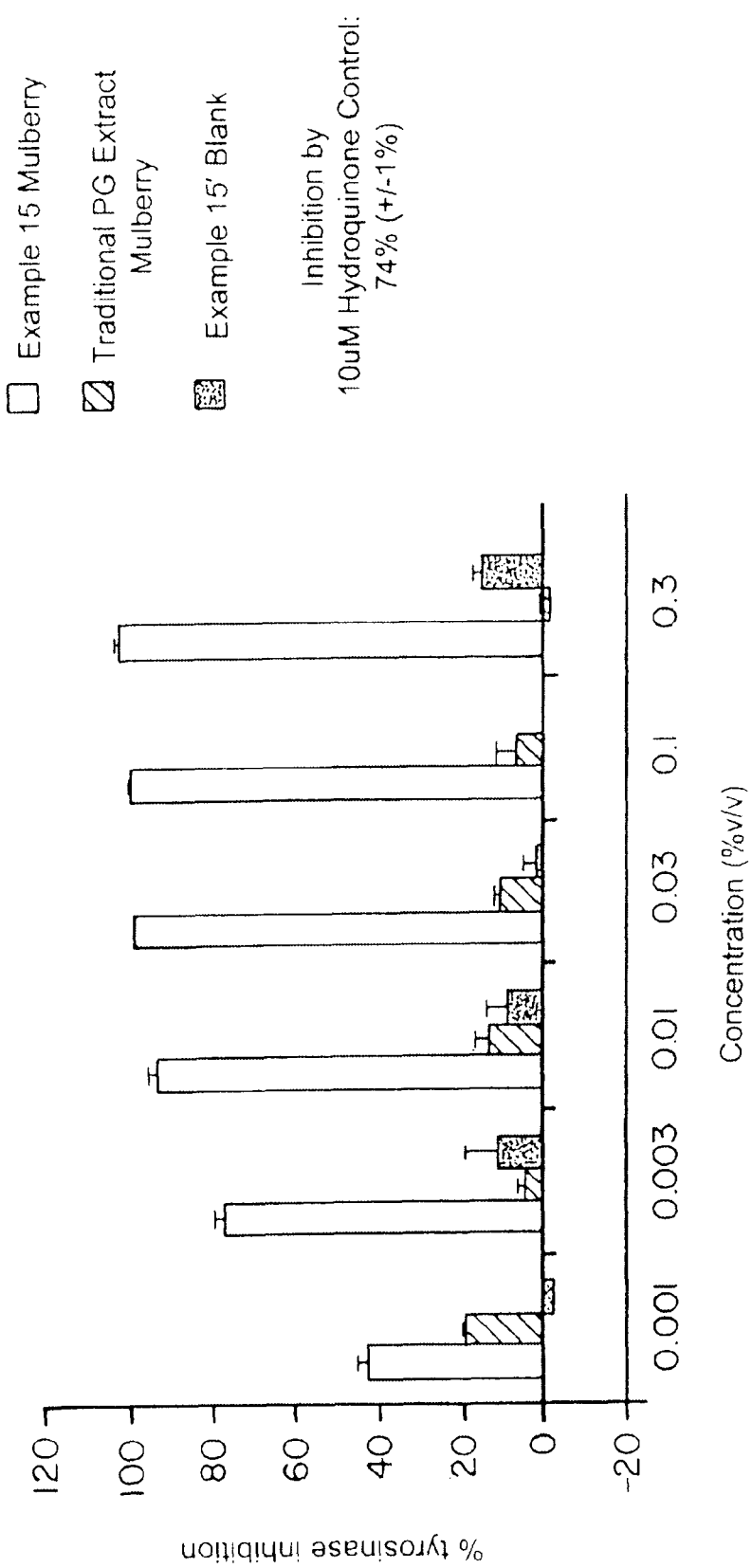
FIG. 3 depicts the tyrosinase inhibitory activity of Example 15, comprising both the polar and apolar solvent soluble organic components of mulberry.

As shown in FIG. 3, the resulting Mulberry extract composition (Example 15) is enriched with powerful tyrosinase inhibitors making it an ideal ingredient in skin whitening products. HPLC chromatograms show, as predicted by the literature, that the dispersion of Example 15 contains a vast array of different polar solvent soluble and apolar solvent soluble compounds. The apolar solvent soluble compounds are being effectively extracted into the silicone oil and are therefore present in the resulting Mulberry extract composition.

Licorice (*glycyrrhiza glabra*) Root Extract

The Licorice extract composition of the invention was prepared from two phases; a hydrophobic phase containing the apolar solvent soluble materials in Licorice root and a hydrophilic phase containing the polar solvent soluble materials.

In Example 3, a silicone based Licorice extract was prepared. Licorice root powder was contacted with silicone oil and subject to stirring. The resulting composition was filtered to clarity.

In Example 9, polar solvent soluble materials were obtained derived from Licorice. Licorice powder was extracted by contacting licorice with propylene glycol and constant stirring for 5 hours at room temperature. The resulting composition was diluted with water and Germazide™ MPB was added.

Figure 4:
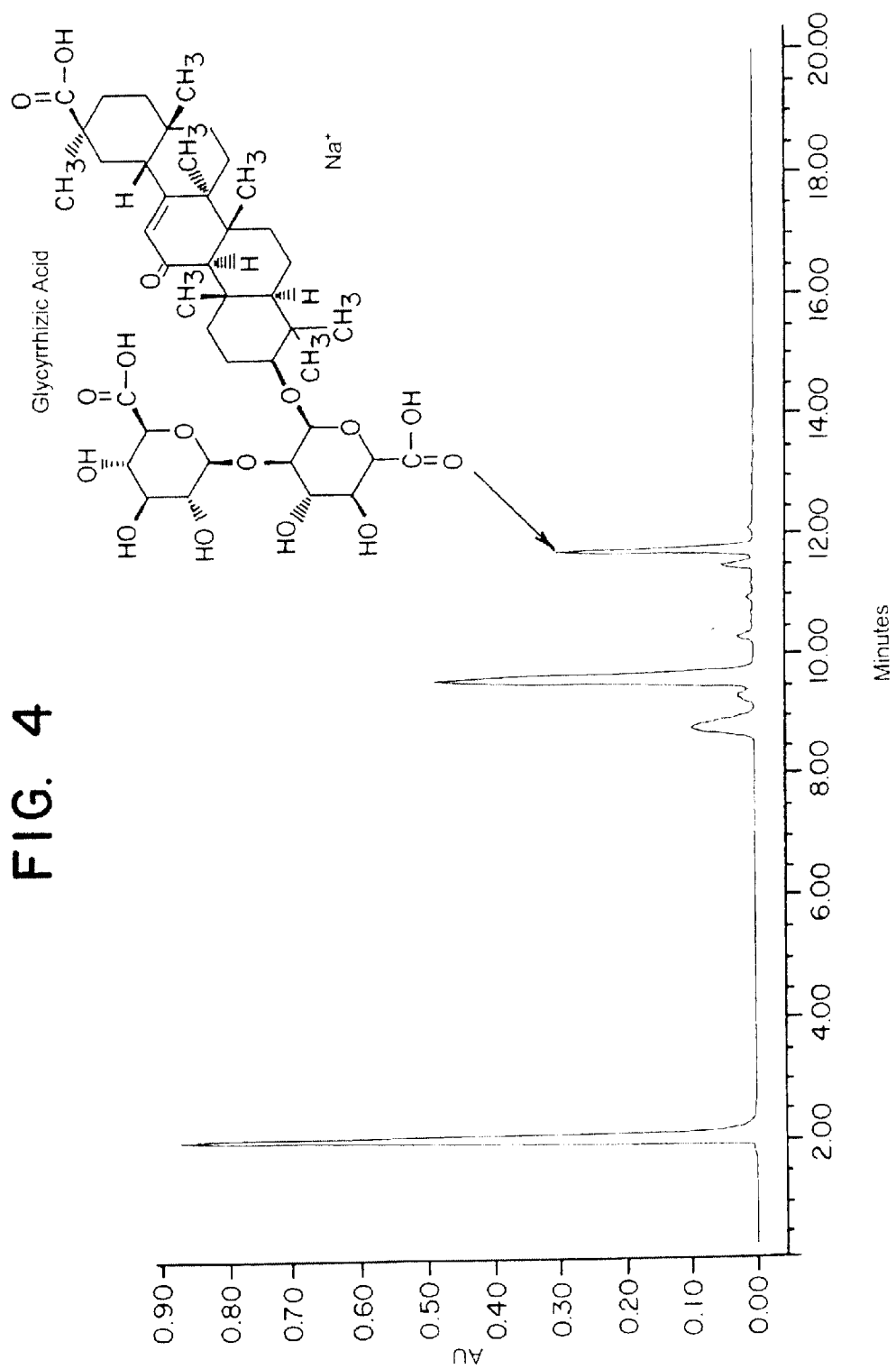
FIG. 4 is a chromatogram of a composition containing the apolar solvent soluble components of licorice.
Figure 5:
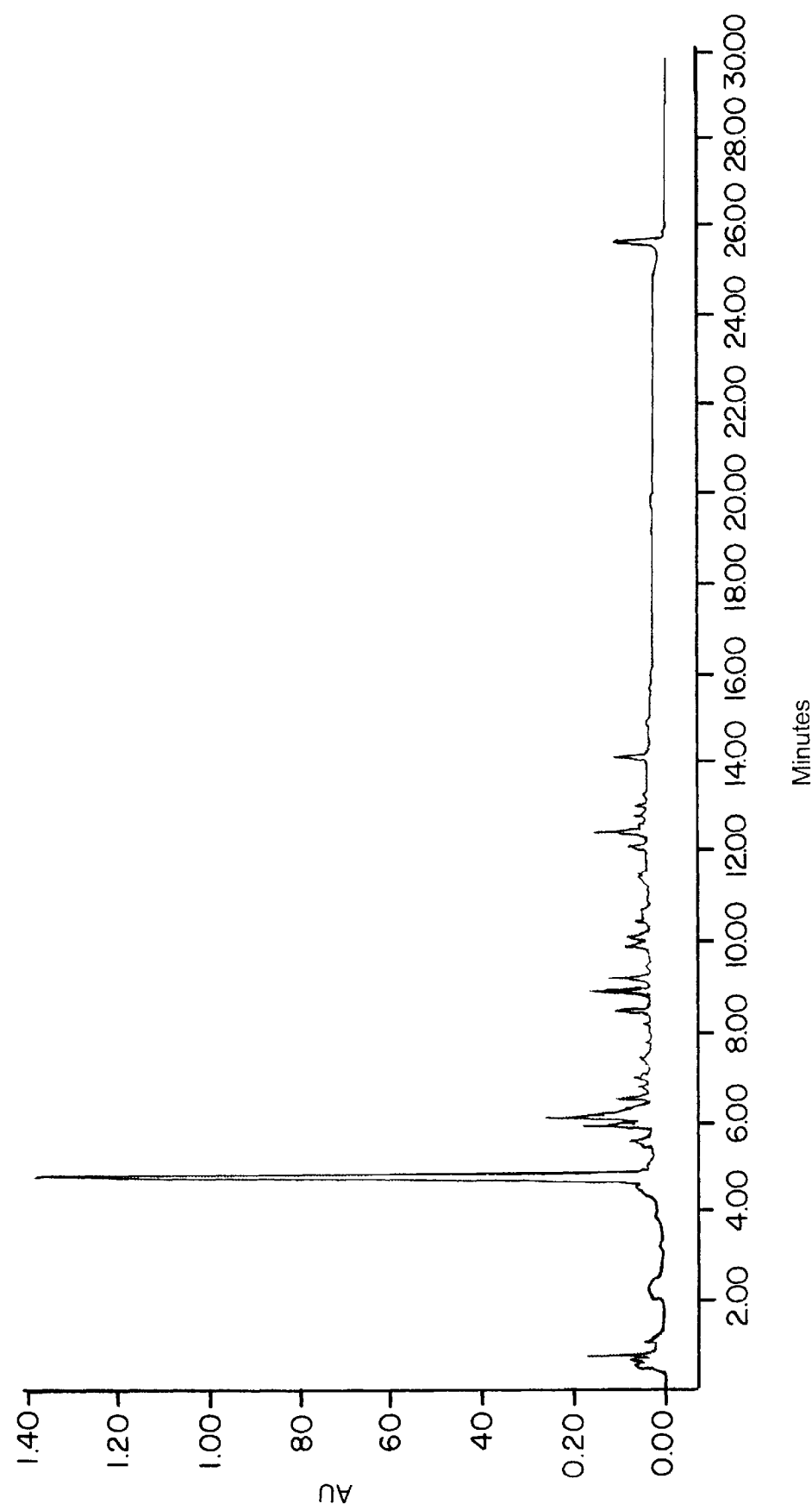
FIG. 5 is a chromatogram of a composition containing the polar solvent soluble components of licorice.

The HPLC trace for silicone and aqueous extracts of licorice is shown in FIGS. 4 and 5. Glycyrrhizic acid has been identified and is labeled. FIGS. 4 and 5 show that the Licorice extract composition of the invention contains a vast array of different compounds. The chromatograms were run using different wavelengths solvent systems so it is misleading to compare them directly. The size of the peak heights for Gylcyrrhizic acid are different because of the different wavelengths. However, the peaks can be clearly seen in both chromatograms.

The two phases were mixed together along with phospholipid in a high shear mixer and then combined them using high pressure, high shear processing to produce the dispersion of Example 17, containing both the polar and apolar solvent soluble organic components of licorice.

Figure 6:
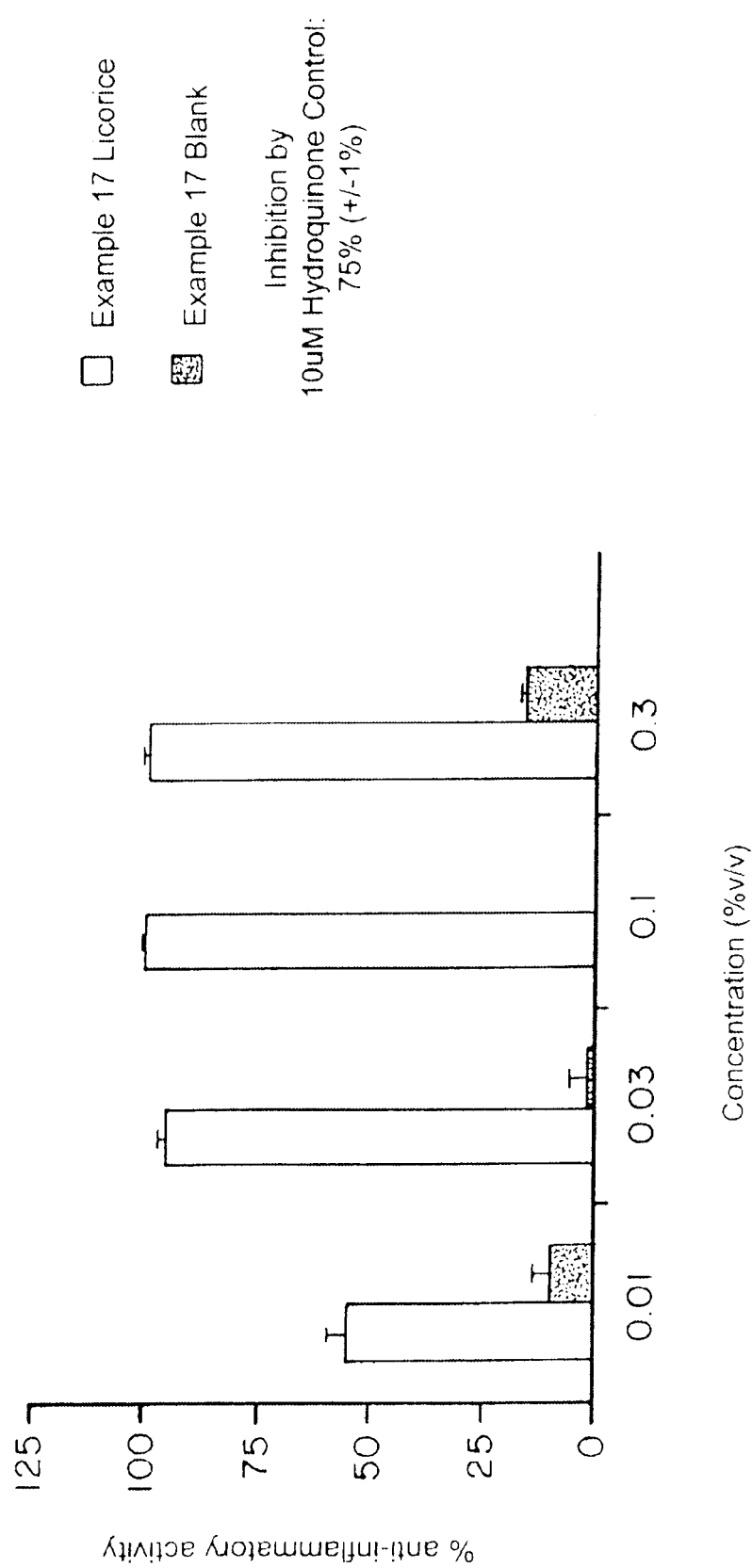
FIG. 6 depicts the tyrosinase inhibitory activity of Example 17, comprising both the polar and apolar solvent soluble organic components of licorice.
Figure 7:
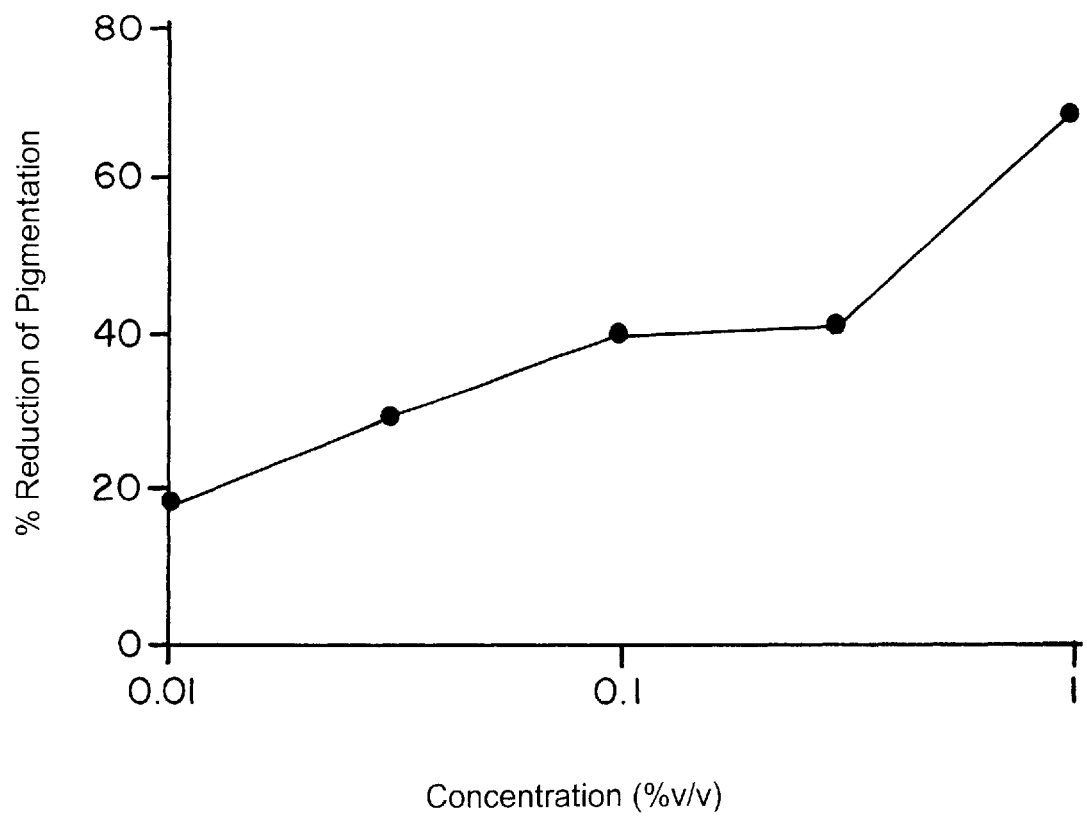
FIG. 7 depicts the melanocyte pigmentation reduction of Example 17, comprising both the polar and apolar solvent soluble organic components of licorice.

FIGS. 6 and 7 depict the tyrosinase inhibiting activity and melanocyte pigmentation reduction activity, respectively, of the licorice extract composition of Example 17. As shown in FIG. 6, licorice extract contains powerful tyrosinase inhibitors. The effect of these inhibitors can be demonstrated by either direct tyrosinase inhibition or by measuring the reduction of melanocyte pigmentation. The licorice extract composition of the present invention is also an antioxidant, making it an ideal ingredient for skin whitening products.

In addition, a melanocyte pigmentation assay was conducted for the composition of Example 17. Results of the assay are depicted below.

TABLE 4

Melanocyte Pigmentation Reduction of Example 17

| ID | conc. | Culture pigmentation (OD$_{405}$nm) mean | SE | SD | CV % | % inhibition | p* |
|---|---|---|---|---|---|---|---|
| Example 17 Licorice (%) | 1 | 0.327 | 0.004 | 0.007 | 2 | 68 | 0.00003 |
|  | 0.3 | 0.610 | 0.015 | 0.026 | 4 | 41 | 0.0003 |
|  | 0.1 | 0.621 | 0.024 | 0.042 | 7 | 40 | 0.0005 |
|  | 0.03 | 0.729 | 0.017 | 0.029 | 4 | 29 | 0.001 |
|  | 0.01 | 0.842 | 0.009 | 0.016 | 2 | 18 | 0.005 |
| untreated | — | 1.032 | 0.032 | 0.055 | 5 | 0 |  |
| hydroquinone μm | 30 | 0.747 | 0.013 | 0.023 | 3 | 28 | 0.001 |

The ID "untreated" refers to a composition which does not contain any of the organic components of the licorice extract, and thus is a control.

FIG. 7 depicts the results of the melanocyte pigmentation reduction of Example 17. Example 17 has an EC$_{50}$ of 0.53% in this assay (see Table 4 and FIG. 7). It is therefore a potent agent for reducing pigmentation and skin whitening.

Lavender (*lavandula angustifolia*) Extract

Lavender extract compositions of the invention were obtained.

In Example 2, a silicone based lavender extract was prepared by contacting lavender with silicone oil and mixing. The resulting composition was filtered to clarity. In Example 8, the polar solvent soluble components of lavender were obtained by contacting lavender with propylene glycol with constant stirring for 5 hours at room temperature. The resulting composition was diluted with water, and Germazide™ MPB was added.

Figure 8:
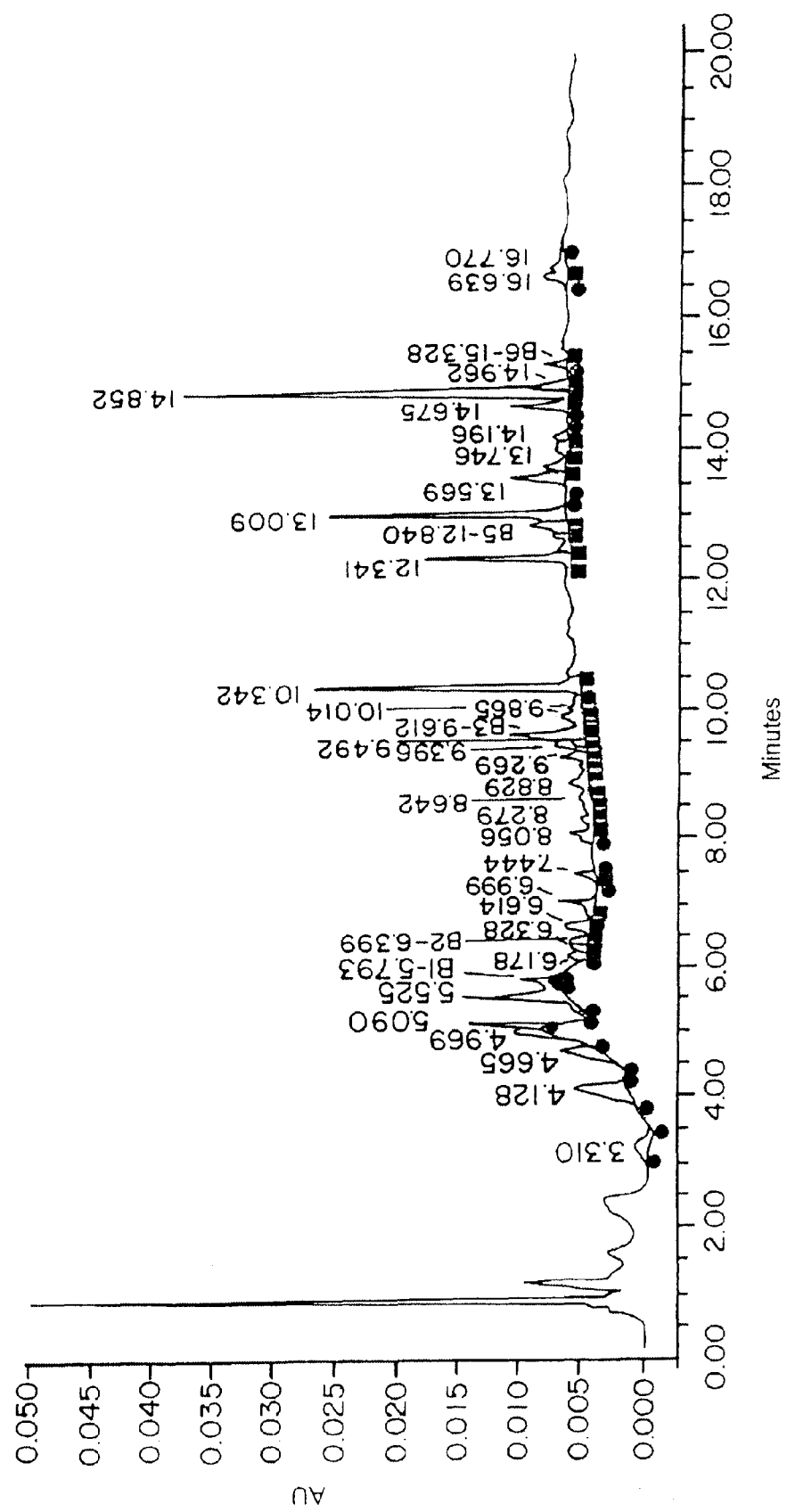
FIG. 8 is a chromatogram of a composition containing the polar solvent soluble components of lavender.
Figure 9:
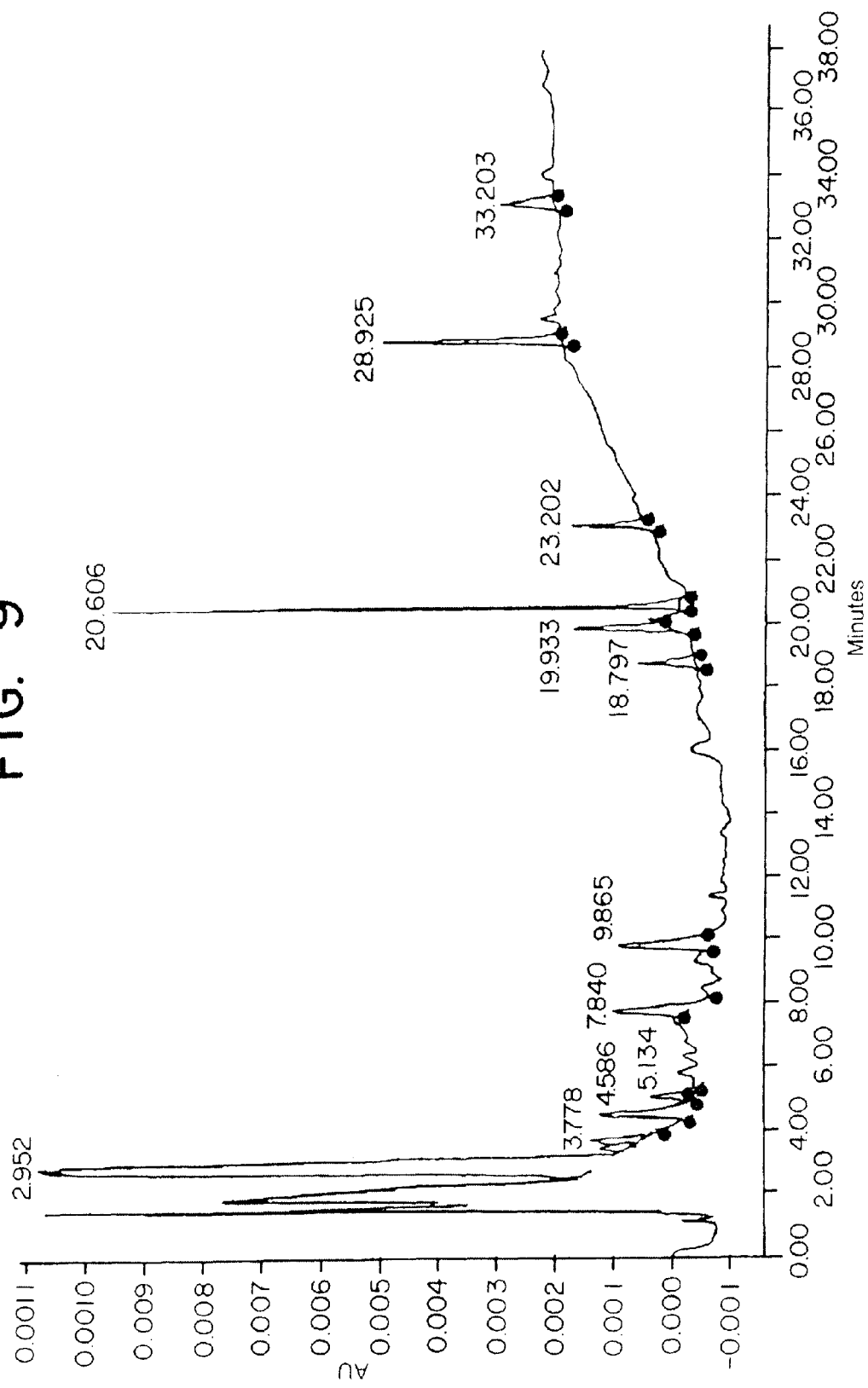
FIG. 9 is a chromatogram of a composition containing the apolar solvent soluble components of lavender.

FIGS. 8 and 9 depict the chromatograms of a water soluble extract and oil soluble extract, respectively, of a lavender extract composition prepared according to the invention.

The two phases were mixed together with phospholipid in a high shear mixer and then combined using high pressure, high shear processing to produce the dispersion of Example 16, containing both the polar and apolar solvent soluble organic components of lavender. The dispersion of Example 16 combines the oil-soluble actives, mainly linalool and linalyl acetate, with the polar solvent soluble flavonoids to produce a powerful combination that will relax, balance and soothe.

Elastin is the structural protein that is predominately responsible for the skin's natural elasticity. This elasticity is gradually lost as skin ages or if skin is damaged because elastin is slowly removed through the action of the enzyme elastase. If this enzyme is too active (such as in inflamed skin) the rate of degradation exceeds the rate of synthesis and the skin quickly looses its suppleness. Cosmetics that inhibit elastase will therefore help improve skin, reduce some of the damaging effects of inflammation and keep skin looking younger for longer.

Figure 10:
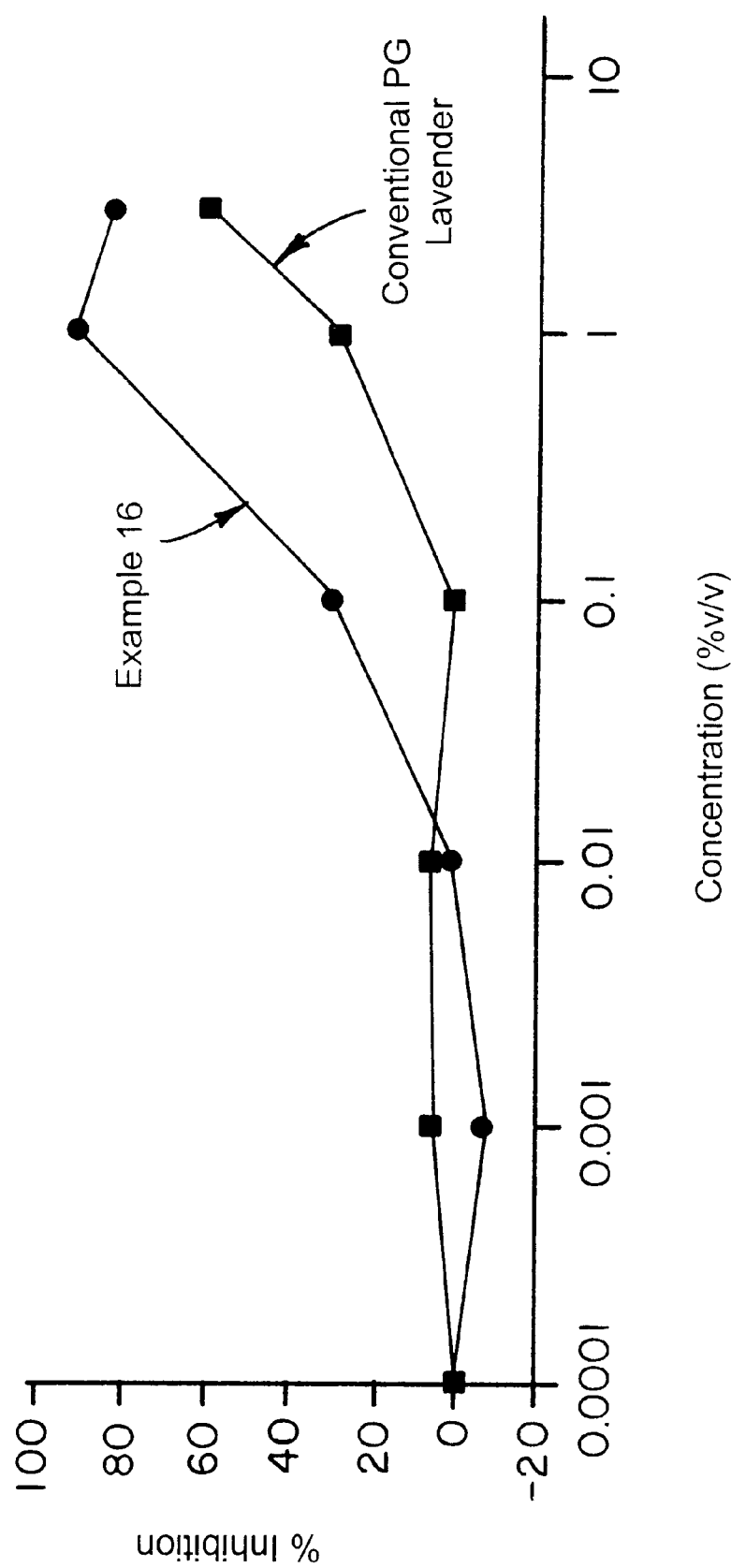
FIG. 10 depicts the results of a neutrophil elastase inhibition assay of Example 16, containing both the polar and apolar solvent soluble organic components of lavender, and a comparison with the assay results for conventional prostaglandin.

FIG. 10 shows elastase inhibition by lavender extract and conventional polyethylene glycol ("PG") extract. Both these extracts inhibit elastase, however the lavender extract composition of the invention is the better inhibitor. Elastase inhibitors in lavender are water-soluble and so it was expected that both the conventional PG and the composition of the invention would show similar inhibition.

The Example 16 dispersion has the activities necessary to maintain normal skin and balance combination skin. It is a strong elastase inhibitor, which helps to maintain skin's elasticity and youthfulness. By inhibiting elastase, the Example 16 dispersion also reduces some of the negative effects of inflammation. The anti-inflammatory properties of Lavender are well supported by published articles. The data described herein demonstrates that Lavender may have weak anti-inflammatory properties that calm and sooth skin. In addition, cell renewal benefits of lavender are well supported by published literature. The linalool and linalyl acetate seen in the lavender extract composition of the invention are known to be antiseptic. These properties of Lavender extract make the Example 16 dispersion ideal for normal and combination skin.

Table 5 contains the results of the Extra Cellular Matrix Degradation assay. The Example 16 dispersion showed some slight anti-inflammatory activity at the highest concentration tested (3%). These results indicate that the level of a stronger anti-inflammatory activity is associated with concentrations of lavender extracts of greater than 3%.

TABLE 5

Results of the Extra Cellular Matrix Degradation Assay of Example 164

| ID | Conc. (% v/v) | ECM degradation by activated neutrophils mean | SE | % anti-inflammatory activity |
|---|---|---|---|---|
| Example 16 (Lavender) | 3 | 40 | 1 | 30 |
|  | 1 | 58 | 1 | −3 |
|  | 0.3 | 56 | 2 | 2 |
|  | 0.1 | 54 | 1 | 5 |
|  | 0 | 57 | 0.5 | 0 |
| Conventional PG Lavender | 3 | 54 | 0 | 5 |
|  | 1 | 54 | 1 | 6 |
|  | 0.3 | 55 | 1 | 3 |
|  | 0.1 | 54 | 1 | 5 |
|  | 0 | 57 | 0.5 | 0 |
| Assay Controls |  |  |  |  |
| No neutrophils (spontaneous leeching of radiolabeled material from ECM) |  | 9 | 0.4 | — |
| Neutrophils (degradation of ECM by unactivated neutrophils) |  | 27 | 1 | — |
| Activated Neutrophils (degradation of ECM by neutrophils that have been activated with phorbol ester) |  | 57 | 0.5 | — |
| Activated Neutrophils + 3% ExCyte ™ Heather (degradation of ECM by activated neutrophils in presence of ExCyte ™ Heather (positive control for inhibition of matrix degradation)) |  | 13 | 1 | 77 |

ExCyte™ Heather is a skin care formulation containing water, glycerin and *calluna vulgaris* extract, available from Collaborative Laboratories of Stony Brook, N.Y.

Arnica Extract

Arnica extract compositions of the invention were prepared. In Example 4, silicone based arnica extract was prepared by contacting arnica with silicone oil and mixing. The resulting composition was filtered to clarity. In Example 10, a polar solvent soluble materials of arnica were obtained by contacting with propylene glycol with constant stirring for 5 hours at room temperature. The resulting composition was diluted with water, and Germazide™ MPB was added. The two phases were mixed together with phospholipid in a high shear mixer and then combined using high pressure, high shear processing to produce the dispersion of Example 18, containing both the polar and apolar solvent soluble organic components of arnica.

Figure 11:
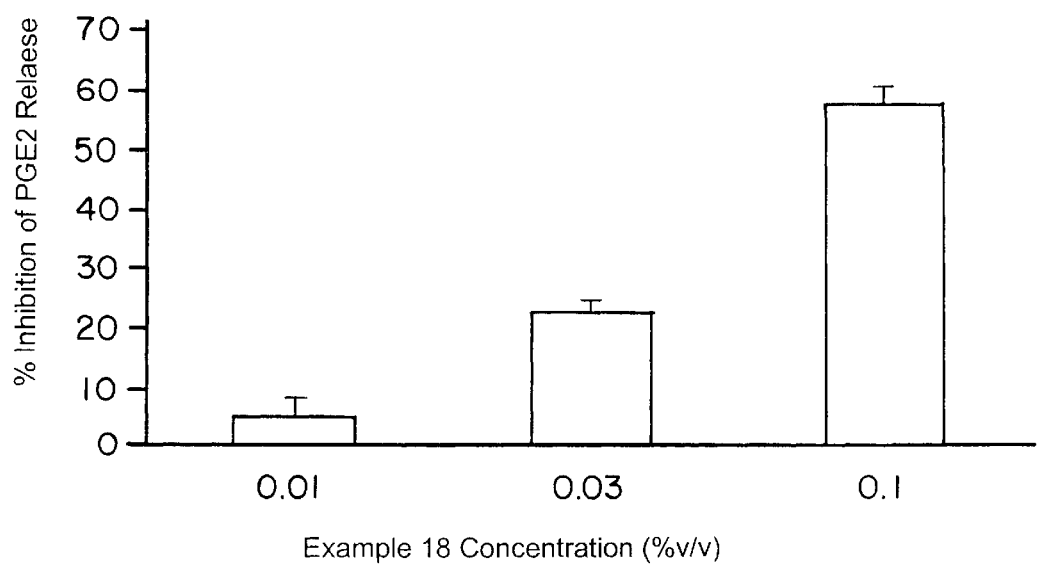
FIG. 11 depicts the results of inhibition of UV-induced $PGE_2$ release of Example 18, containing both the polar and apolar solvent soluble organic components of arnica.

The dispersion of Example 18 was tested for anti-inflammatory activity. The results of the testing are depicted in FIG. 11.

Eyebright (*euphrasia officinalis*)

An Eyebright extract composition of the invention contains both the oil-soluble and water-soluble components of the plant, and thus is very similar to the traditional compresses. The only components missing that are present in the plant itself are insoluble fibrous materials. The Eyebright extract composition of the invention is therefore more effective than conventional Eyebright extracts that normally consist of either the water extractable material or the oil extractable material.

An eyebright extract dispersion was prepared. In Example 5, a silicone eyebright extract was prepared by contacting with silicone oil and mixing. The resulting composition was filtered to clarity. In Example 11, a polar solvent soluble material derived from eyebright was prepared contacting with propylene glycol with constant stirring for 5 hours at room temperature. The resulting composition was diluted with water, and Germazide™ MPB was added.

Figure 12:
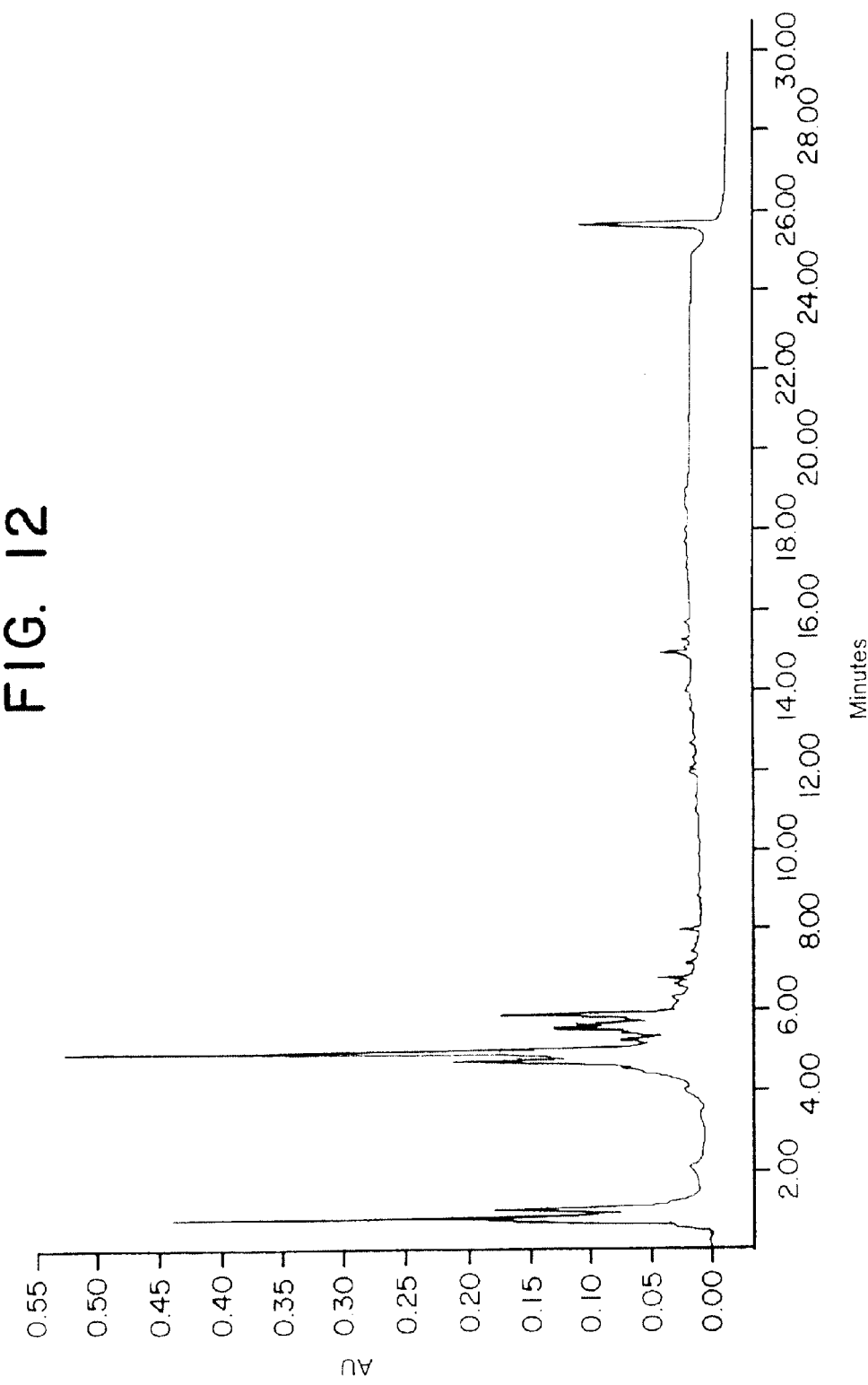
FIG. 12 is a chromatogram a composition containing the polar solvent soluble components of eyebright.
Figure 13:
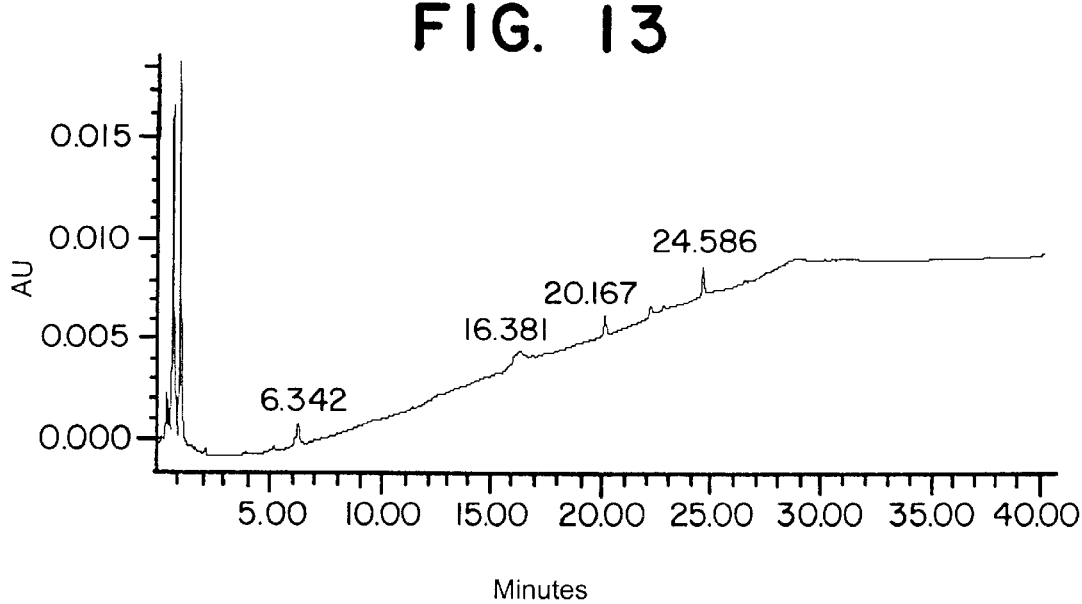
FIG. 13 is a chromatogram of a composition containing the apolar solvent soluble components of eyebright.

FIGS. 12 and 13 depict the chromatograms of polar solvent soluble (Example 11) and apolar solvent soluble extract (Example 5) compositions.

The two phases were mixed together with phospholipid in a high shear mixer and then combined using high pressure, high shear processing to produce the dispersion of Example 19, containing both the polar and apolar solvent soluble organic components of eyebright.

Figure 14:
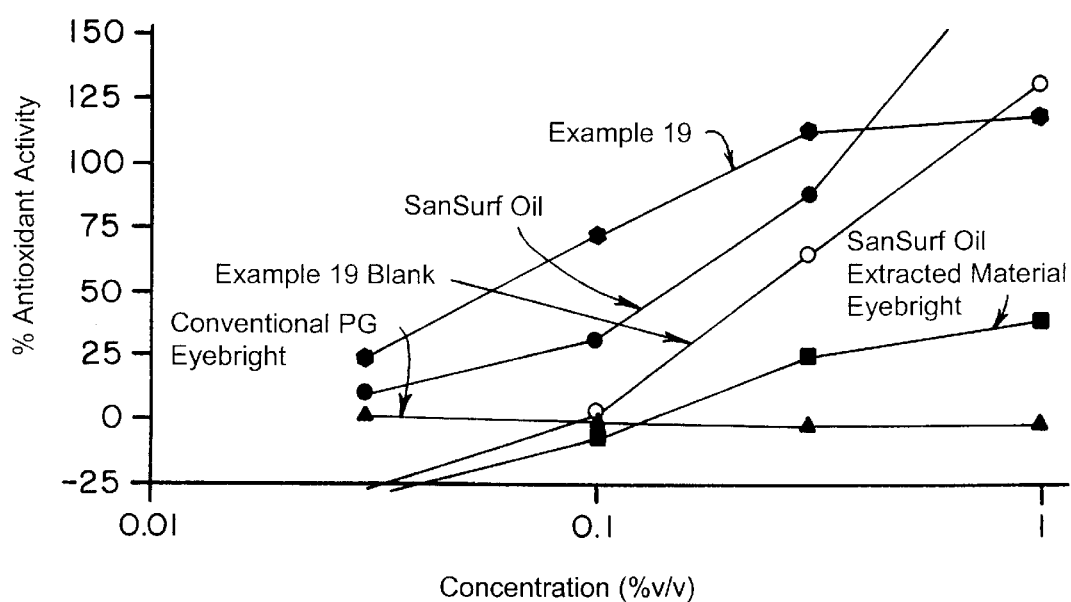
FIG. 14 depicts the results of a cytochrome C reduction assay of Example 19, containing both the polar and apolar solvent soluble organic components of eyebright.

FIG. 14 depicts the results of a cytochrome c reduction assay of the eyebright extact composition of the invention, in comparison with Sansurf™ oil extracted material, a surfactant-free dispersion of lipophilic materials in water, manufactured by Collaborative Laboratories of Stony Brook, N.Y.; conventional PG eyebright; and control compositions of the composition of the invention and Sansurf™. The Eyebright extract composition of the invention showed significant activity at the 0.1% concentration. In contrast, the blanks at 0.1% did not have antioxidant activity. The Eyebright extract composition of the invention performs better than the other materials tested at all concentrations up to 0.5% . The apparent activities seen at higher concentrations are most likely as a result of artifacts such as light scatter. The Example 19 $EC_{50}$ Eyebright extract composition of the invention in the Cytochrome c Reduction assay was 0.07% showing that at this concentration the composition of the invention is a strong antioxidant.

Lipid Peroxidation Assay was carried out to alleviate the concerns raised about the antioxidant activity measured in the Cytochrome c reduction assay. It has been suggested that this assay may be influenced by factors other than oxidation. The results for the Example 19 composition in the Lipid Peroxidation assay are shown in Table 6.

TABLE 6

Results of the Lipid Peroxidation Assay of Eyebright Compositions

| Sample ID | conc. % | $OD_{532}$ at indicated time (min) | | | | Rate of Lipid Peroxidation ($MOD_{532}$/min) | % antioxidant effect |
|---|---|---|---|---|---|---|---|
| | | 0 | 60 | 120 | 240 | | |
| Example 19 Eyebright | 1 | 0.018 | 0.020 | 0.021 | 0.029 | 46 | 84 |
| | 0.2 | 0.013 | 0.018 | 0.028 | 0.073 | 257 | 12 |
| | 0.04 | 0.014 | 0.026 | 0.056 | 0.088 | 320 | −9 |
| SanSurf™ Oil Extracted Material | 1 | 0.014 | 0.035 | 0.060 | 0.100 | 360 | −23 |
| | 0.2 | 0.013 | 0.030 | 0.062 | 0.105 | 396 | −35 |
| | 0.04 | 0.014 | 0.030 | 0.059 | 0.107 | 395 | −35 |
| Conventional PG Eyebright | 1 | 0.014 | 0.028 | 0.058 | 0.109 | 410 | −40 |
| | 0.2 | 0.013 | 0.031 | 0.061 | 0.105 | 390 | −33 |
| | 0.04 | 0.013 | 0.034 | 0.066 | 0.109 | 407 | −39 |
| Example 19 Blank | 1 | 0.020 | 0.048 | 0.074 | 0.111 | 375 | −28 |
| | 0.2 | 0.014 | 0.034 | 0.062 | 0.108 | 397 | −35 |
| | 0.04 | 0.015 | 0.030 | 0.059 | 0.099 | 359 | −23 |
| SanSurf™ Oil Extract Material Blank | 1 | 0.020 | 0.025 | 0.057 | 0.105 | 377 | −29 |
| | 0.2 | 0.017 | 0.024 | 0.056 | 0.104 | 381 | −30 |
| | 0.04 | 0.017 | 0.026 | 0.055 | 0.111 | 408 | −39 |
| Vitamin C | 0.3 | 0.011 | 0.012 | 0.013 | 8 | 97 | |
| | 0.3 | 0.011 | 0.011 | 0.011 | 0.012 | 3 | 99 |
| | 0.03 | 0.012 | 0.013 | 0.016 | 0.025 | 54 | 82 |
| | 0.03 | 0.014 | 0.0125 | 0.014 | 0.0205 | 30 | 90 |
| untreated | — | 0.013 | 0.013 | 0.015 | 0.023 | 293 | — |

The blanks listed above contain all the elements of the composition without the organic components of the natural products.

The $EC_{50}$ for the Eyebright extract dispersion of Example 19 for lipid peroxidation was found to be 0.6% . The Example 19 dispersion is therefore a strong antioxidant while the SanSurf™ Oil Extracted Material, the Conventional PG Eyebright and the blank composition of the invention did not significantly prevent the production of malondialdehyde at any of the concentrations tested and therefore have no antioxidant properties.

Grape Root (*mahonia aquifolium*)

A Grape Root extract composition of the invention was prepared.

In Example 6, a silicone based Grape Root extract is prepared. Grape Root was extracted by contacting with silicone oil and mixing. The resulting composition was filtered to clarity. In Example 12, a polar solvent soluble material derived from Grape Root is prepared. Grape Root was extracted by contacting with propylene glycol with constant stirring for 5 hours at room temperature. The resulting composition was diluted with water, and Germazide™ MPB was added. The two phases were mixed together with phospholipid in a high shear mixer and then combined using high pressure, high shear processing to produce the dispersion of Example 20, containing both the polar and apolar solvent soluble organic components of grape root.

Figure 15:
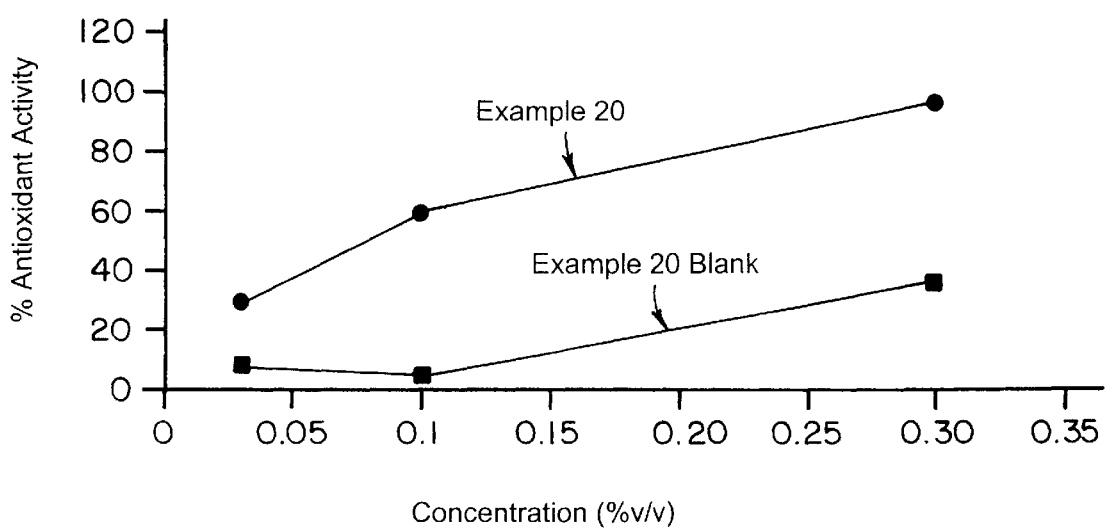
FIG. 15 depicts the results of a cytochrome C reduction assay of Example 20, containing both the polar and apolar solvent soluble organic components of grape root.

FIG. 15 depicts the results of a cytochrome C reduction assay of Example 20. These results demonstrate that the Grape Root extract dispersion of the invention (Example 20) is an effective antioxidant at concentrations of 0.08%.

The following assays were used for testing the properties of the natural product extracts of the invention.

Antioxidant Assays
Cytochrome C Reduction Assay
Materials

Citrate-phosphate-dextrose solution ("CPD"; C-7165), sodium chloride (NaCl; S-5886); phosphate-buffered saline (PBS; 1000-3), cytochrome c (C-7752), phorbol 12-myristate 13-acetate ("PMA"; P8139), superoxide dismutase ("SOD"; S-5395) and staurosporine ("STA"; S-4400) were obtained from Sigma. Hank's balanced salt solution ("HBSS"; 14025-035) and Lymphoprep™ 1.077 were obtained from Gibco BRL. Dextran T-500 (17-0320-01) was obtained from Pharmacia. Wright's stain (LeukoStat™ stain kit) was obtained from Fisher (CS-430). Optical densities were determined using a Dynatech MR5000 spectrophotometer.

Methods

Polymorphonuclear leukocytes (neutrophils or "PMN") were isolated using standard procedures. Blood was drawn from healthy donors using citrate-phosphate-dextrose as an anticoagulant. An equal volume of 3% Dextran in 0.9% NaCl was added to settle the majority of erythrocytes. After 20 minutes incubation, the cleared top layer was harvested and centrifuged at 250×g for 10 minutes. The cell pellet was resuspended in 0.9% NaCl, layered onto Lymphoprep™ and centrifuged at 40×g for 40 minutes. The resulting pellet was then subjected to several cycles of hypotonic lysis (typically 3 cycles) to remove residual erythrocytes. Each lysis cycle involved resuspension of the cell pellet in ice-cold 0.2% NaCl for 30 seconds, restoration of isotonicity by the addition of an equal volume of 1.6% NaCl, followed by centrifugation at 250 g for 10 minutes at 4° C. When the erythrocyte removal was complete, the PMN were resuspended in PBS and stored at 4° C. until required. Purity of the preparation was checked by staining a cell smear with Wright's stain.

Lipid Peroxidation Assay
Materials

Thiobarbituric acid ("TBA"; T5500), sodium dodecyl sulfate (L4509), butylated hydroxytoluene (B1378), glycine (G7126) and phosphate-buffered saline ("PBS"; 1000-3) were obtained from Sigma. Lecithin (429415) was obtained from Calbiochem. Ethanol (122898) was obtained from Aaper Alcohol and Chemical Co. Vitamin C (95209) was obtained from Fluka. Ferric chloride (AR5029) was obtained from Mallinckrodt. Optical densities were determined using a SpectraMax 250 spectrophotometer (Molecular Devices). Ultraviolet irradiation was performed using a model VWR M-20E Chromato-Vue transilluminator (VWR Scientific).

Methods

The Lipid Peroxidation assay measures inhibition of UV-induced lipid oxidation. The reaction was performed at room temperature by irradiating liposome solutions, containing varying concentrations of test samples, with ultraviolet C light.

The extent of lipid peroxidation induced by the UV light was determined by measuring the consequent production of malondialdehyde that results from breakdown of oxidized lipid. Irradiated liposome solutions contained 0.8% lecithin and 18% ethanol in PBS, along with test sample or control. Vitamin C, a peroxyl radical scavenger, was included in each assay as a control for inhibition of lipid oxidation. Duplicate aliquots of the irradiation mixtures were harvested at several time points and their malondialdehyde contents were measured using the "thiobarbituric acid reaction". TBA reaction mixtures contained 300 $\mu$M butylated hydroxytoluene, 300 $\mu$M $FeCl_3$, 16 mM TBA, 0.14% sodium dodecyl sulfate, 90 $\mu$M glycine (pH 3.6) and 3% (v/v) irradiation mixture aliquot. The mixtures were heated at 100° C. for 15 minutes, cooled to room temperature and their absorbencies were read at 532 and 650 nm. The readings at 650 nm were subtracted from those at 532 nm to correct for turbidity. These corrected absorbencies were plotted as a function of irradiation time and the rate of lipid peroxidation was determined by linear regression curve fit. An $EC_{50}$ (the concentration of test sample that inhibits 50% of the rate of lipid peroxidation) was calculated for each sample.

Anti-Inflammation Assay
Extra Cellular Matrix Degradation (ECM) Assay
Materials

Ammonium hydroxide (A-6899), streptomycin sulfate (S-0890) citrate-phosphate-dextrose solution ("CPD"; C-7165), sodium chloride (NaCl; S-5886); phosphate-buffered saline (PBS; 1000-3),phorbol 12-myristate 13-acetate ("PMA"; P8139), and sodium azide (S-8032) were obtained from Sigma. Minimal Essential Medium ("MEM"; 11095-072), tryptose phosphate (18050-013) heat-inactivated fetal bovine serum ("FBS"; 10082-147) Hank's balanced salt solution ("HBSS"; 14025-035) and Lymphoprep™ 1.077 were obtained from Gibco BRL. R-22 cells were obtained from Dr. S. Simon (Dept. of Pathology, SUNY Stony Brook). Dextran T-500 (17-0320-01) was obtained from Pharmacia. Wright's stain (LeukoStat™ stain kit) was obtained from Fisher (CS-430). ExCyte™ Heather was obtained from Collaborative Laboratories.

For the production of radiolabeled ECM plates, R-22 smooth muscle cells were seeded into 24-well plates and grown in maintenance medium (MEM containing 10% FBS, 2% tryptose phosphate, 100 $\mu$g/ml streptomycin). Upon reaching confluence, the cells were switched into labeling medium (maintenance medium supplemented with 50 mg/ml ascorbic acid and 0.5 $\mu$Ci/ml L-[2,3,4,5-$^3$H]-proline) and maintained in this medium for 2 weeks. The plates were then harvested by aspirating the labeling medium and lysing the cells by 5 minute incubation in 25 mM ammonium hydroxide followed by 3 cycles of 5 minute incubation in sterile deionized water. Prior to use, the plates were stored at 4° C. with 50 $\mu$l/well of 0.02% sodium azide.

Polymorphonuclear leukocytes (neutrophils or "PMN") were isolated using standard procedures. Blood was drawn from healthy donors using citrate-phosphate-dextrose as anticoagulant. An equal volume of 3% Dextran in 0.9% NaCl was added to settle the majority of erythrocytes. After 20 minutes incubation, the cleared top layer was harvested and centrifuged at 250×g for 10 minutes. The cell pellet was resuspended in 0.9% NaCl, layered onto Lymphoprep™ and centrifuged at 400×g for 40 minutes. The resulting pellet was then subjected to several cycles of hypotonic lysis (typically 3 cycles) to remove residual erythrocytes. Each lysis cycle involved resuspending the cell pellet in ice-cold 0.2% NaCl for 30 seconds, restoration of isotonicity by addition of an equal volume of 1.6% NaCl, followed by centrifugation at 250 g for 10 minutes at 4° C. When erythrocyte removal was complete, the PMN were resuspended in PBS and stored at 4° C. until use. Purity of the preparation was checked by staining a cell smear with Wright's stain.

Methods

For the ECM degradation assay, radiolabeled ECM plates were washed 3 times with HBSS to remove azide. To start the degradation reaction, 1 ml of HBSS containing 5 nM PMA, 1×10$^6$ PMN, and the indicated test sample concentration was added to 3 wells of an ECM plate. In each assay, there were also 4 control conditions (triplicate wells for each). These were HBSS alone (to correct for leeching of unincorporated radiolabel), cells in HBSS (to monitor degradation by "unstimulated"PMN), cells in HBSS with 5 nM PMA (maximal stimulated matrix degradation), and cells in HBSS with 5 nM PMA and 3% ExCyte™ Heather (positive control for inhibition of matrix degradation), available from Collaborative Laboratories. Upon addition of reaction mixtures, the plates were incubated at 37° C. for 4 hours. ECM degradation in each well was scored by scintillation counting to measure radioactivity released into the supernatant as well as that remaining in the residual matrix. Using these 2 measures, the % ECM degradation was calculated for each well. An $EC_{50}$, the concentration of test sample that decreased ECM degradation by 50% relative to the maximal stimulated matrix degradation condition, was calculated where possible.

Elastase Inhibition Assay

Materials

Tris[hydroxymethyl]aminomethane ("Tris"; T-1410), sodium chloride (NaCl; S-5886), dimethyl sulfoxide ("DMSO"; D-8779), sodium acetate (S-8625) and hydrochloric acid ("HCl"; H-7020) were obtained from Sigma. Human neutrophil elastase ("HNE"; 16-14-051200) was obtained from Athens Research. Methoxysuccinyl-lAAPVpNA ("peptide"; L-1335) was obtained from Bachem. Optical densities were determined using a Dynatech MR5000 spectrophotometer.

Methods

The assay was performed in a 96-well plate with triplicate wells for each reaction condition. Reaction mixtures contained 63 mM Tris-HCl (pH 8.0), 195 mM NaCl, 5 mM sodium acetate, 1.5% DMSO, 300 µg/µl peptide, 1.5 µg/µl HNE and test sample as indicated. The reaction was started by addition of HNE and followed by measuring $A_{405}$ at minute intervals for 10 minutes. The reaction rate was determined from the slope of a straight line fitted to the data plot.

Inhibition of UV-Induced $PGE_2$ production

This assay measures production of $PGE_2$ by keratinocytes exposed to UVB radiation.

Materials

HaCaT cells, a spontaneously immortalized human keratinocyte line (Boukamp et al, J Cell Biology 106 (1988) 761–771), were obtained from Dr. Norbert Fusenig (German Cancer Research Center). Tris[hydroxymethyl] aminomethane (T-1410), sodium chloride (S-5886), ethylenediaminetetraacetic acid (E-4884), and phosphate-buffered saline ("PBS"; 1000-3), Neutral Red (N-6634) and glucose (G-5400) were obtained from Sigma. Ethanol (A405P-4) was obtained from Fisher Scientific. Acetic acid (AC110) was obtained from Spectrum Chemical Corp. Dulbecco's Modified Eagle's Medium ("DMEM"; 11885-076), heat-inactivated fetal bovine serum ("FBS"; 10082-147), and 5000 units/ml penicillin/5000 µg/µl streptomycin (15070-063) were obtained from Gibco BRL. $PGE_2$ EIA kits (DE0100) were obtained from R&D Systems. UBL model FSX24T12/UVB-HO bulbs (National Biological Corp.) were used for cell irradiation. Bulb output was measured with an International Light Model IL1700 radiometer. Absorbances were measured using a Dynatech MR5000 spectrophotometer.

Methods

Cells were seeded into 12-well plates in DMEM containing 10% FBS, 50 units/ml penicillin and 50 µg/µl streptomycin ("medium"). When the cells were approximately 65% confluent they were switched into medium containing varying concentrations of test samples or indomethacin (positive control for inhibition of $PGE_2$ production). After a 12-hour preincubation, the media were removed and the cells were washed with, and transferred into PBS-glucose (PBS containing 5.5 mM glucose). They were immediately irradiated with 11 mJ/cm$^2$ of UVB (approx. 45 second exposure) and transferred back into media containing the same concentrations of test samples or controls as for the preincubation period. After a further 8 hour incubation, the media were collected and stored at −70° C. After removal of the media, the cells were fed with medium containing Neutral Red dye and incubated at 37° C. for 3 hours. The cells were then washed with buffer and internalized dye was extracted with an ethanol/acetic acid solution. Extracted Neutral Red was determined by measuring its absorbance at 550 nm. The levels of $PGE_2$ in the supernatants were measured using a commercially available EIA kit.

Skin Whitening Assays

Tyrosinase Inhibition Activity

Materials

The following materials were used in the tyrosinase assay:—Tyrosine T8909, Tyrosinase (mushroom) T7755, Hydroquinone H9003, and Sodium Phosphate S7907 and S8282 were obtained from Sigma. Optical density readings were determined using a Dynatech MR5000 spectrophotometer.

Methods

Tyrosinase activity was determined by measuring the rate of change of optical density at 490 nm as tyrosine was converted into dopachrome. (Tyrosinase catalyzes the conversion of tyrosine into DOPA quinone, which spontaneously converts into dopachrome.) The rate of tyrosinase activity in the presence of various concentrations of test sample was measured at room temperature in a reaction mixture containing 50 mM sodium phosphate (pH 6.75), 275 µM tyrosine and 25 U/ml [Is 25U a typographical error?] mushroom tyrosinase. Readings were made at one minute intervals for ten minutes and the reaction rate was calculated by linear regression. Each concentration was run in triplicate. Inhibition of tyrosinase activity was expressed as a percentage of the activity measured for the untreated control mixture (no test sample). An $EC_{50}$ (the concentration of test sample that inhibits 50% of tyrosinase activity) was calculated. Hydroquinone was tested in each assay as a positive control for inhibition of tyrosinase activity.

Melanocyte Pigmentation Assay

Materials

The following materials were used in the melanocyte pigmentation assay. Cloudman S91 cells (36-1-38C8-16) were obtained from American Type Culture Collection. Dulbecco's Modified Eagle's Medium ("DMEM"; 11885-076), heat-inactivated horse serum (26050-088), heat-inactivated fetal bovine serum (10082-147) and 5000 units/ml penicillin/50 µg/ml streptomycin (15070-063) were obtained from Gibco BRL. Phosphate-buffered saline (PBS; 1000-3), dimethyl sulfoxide (D2650), hydroquinone (H9003), α-melanocyte stimulating hormone (M4135), trichloroacetic acid (T9159) and sodium hydroxide (S8045) were obtained from Sigma. Optical densities were determined using a Dynatech MR5000 spectrophotometer.

Methods

The melanocyte pigmentation assay measures a test sample's ability to inhibit pigmentation. Cloudman S91 melanocytes were seeded into multiwell plates in medium (Dulbecco's Modified Eagle's Medium containing 15% heat-inactivated horse serum, 2.5% heat-inactivated fetal bovine serum, 50 units/ml penicillin and 50 µg/ml streptomycin) containing 10 nM µ-melanocyte stimulating hormone and varying concentrations of the test sample or 30

μM hydroquinone (the positive control for inhibition of pigmentation). After a 5-day treatment period with each condition tested in triplicate wells, the cells were harvested by washing with PBS and adding 5% trichloroacetic acid to each well. After a 15 minute incubation the acid was aspirated and replaced with 200 μl/well of 10% dimethyl sulfoxide/1N sodium hydroxide. The plates were sealed and incubated at 65° C. for 30 minutes. 200 μl of each digestion mixture was then transferred to a well of a 96-well microtiter plate and optical densities were read at 405 nm.

Inhibition of pigmentation is expressed as the percentage decrease in optical density compared to that for untreated cells (no test sample or hydroquinone). An $EC_{50}$ (the concentration of test sample that inhibits 50% of pigmentation) was calculated for each sample.

What is claimed is:

1. A stable, homogeneous dispersion comprising
   (a) from about 20 to 90% by weight of a first composition comprising:
      (i) about 60–95% by weight of water;
      (ii) about 0–40% by weight of one or more polar solvents; and
      (iii) water soluble components of a first natural product derived from plants; and
   (b) from about 10 to 60% by weight of a second composition comprising:
      (i) one or more apolar solvents;
      (ii) and oil soluble organic components of a second natural product derived from plants; and
   (c) from about 0.01 to 8% by weight of a non-surface active lipid phosphate or a surface active agent, wherein said first composition and said second composition are subjected to high pressure high shear processing without heat.

2. The dispersion of claim 1 wherein said polar solvent is selected from the group consisting of water; a mono, di, tri or polyhydroxy alkyl derivative; a mono, di, tri or polyhalogenated alkyl derivative; a mono, di, tri or poly alkyl ether derivative; and a mono, di, tri or poly carboxyl alkyl derivative.

3. The dispersion of claim 1, wherein said polar solvent is selected from the group consisting of water, glycerin, sorbitol, propylene glycol, ethylene glycol, butylene glycol, hexylene glycol, acetone, polyethylene oxide, methyl chloride and mixtures thereof.

4. The dispersion of claim 1, wherein said first composition is formed by the steps of extracting water soluble components of said first natural product derived from plants by contacting said first natural product derived from plants with said first polar solvent to form a solution, and optionally thereafter diluting said solution with said one or more second polar solvents.

5. The dispersion of claim 1, wherein said first composition is formed by the steps of extracting water soluble components of said first natural product derived from plants by contacting said first natural product derived from plants with one or more second polar solvents to form a solution, and thereafter diluting said solution with said first polar solvent.

6. The dispersion of claim 1, wherein said first composition is formed by the steps of extracting water soluble components of said first natural product derived from plants by contacting said first natural product derived from plants with said first polar solvent to form a solution, and thereafter diluting said solution with said first polar solvent.

7. The dispersion of claim 1, wherein said first composition is formed by the step of extracting water soluble components of a first natural product derived from plants by contacting said first natural product derived from plants with said first and one or more second polar solvents to form a solution.

8. The dispersion of claim 1 wherein said first composition is about 40 to 80% by weight of said dispersion.

9. The dispersion of claim 8 wherein said first composition is about 60 to 65% by weight of said dispersion.

10. The dispersion of claim 1, wherein said second composition is about 20 to 50% by weight of said dispersion.

11. The dispersion of claim 10, wherein said second composition is about 30 to 40% by weight of said dispersion.

12. The dispersion of claim 11, wherein said second composition is about 30% by weight of said dispersion.

13. The dispersion of claim 1, wherein said apolar solvent is selected from the group consisting of a mono, di, tri or polyalkyl ester or ether of a mono, di, tri or polyhydroxy compound; a saturated, unsaturated, linear, branched, or cyclic hydrocarbon; a saturated, unsaturated, linear or branched $C_8$ to $C_{30}$ fatty acid; a branched, linear, or cyclical silicone or silicone derivative; or a homopolymer or heteropolymer fluid formed by the polymerization of alkylene oxide monomers.

14. The dispersion of claim 13, wherein said apolar solvent is selected from the group consisting of vegetable oil, soybean oil, babasu oil, castor oil, cottonseed oil, grapeseed oil, rice bran oil, canola oil, palm oil, palm kernel oil, olive oil, linseed oil, coconut oil, sunflower oil, safflower oil, peanut oil, corn oil, mineral oil, petrolatum, hydrogenated polyisobutene, permethyl fluids, polyisobutene, polybutene, cyclomethicone, dimethicone polysiloxane, dimethicinol, polysiloxanes, polyalkyl siloxanes, polyarylsiloxanes, polyalkylaryl siloxanes, polysiloxane copolymers, polypropylene oxide, polybutylene oxide, isopropyl palmitate, diisopropyl adipate or mixtures thereof.

15. The dispersion of claim 1, wherein said first or second natural product derived from plants is selected from the group consisting of mulberry, lavender, licorice root, arnica, eyebright and grape root, green tea leaves, rosemary powder, echinacea, evening primrose, sea parsley, calendula and tea tree leaves.

16. The dispersion of claim 1, wherein said first composition is formed by the steps of extracting water soluble components of said first natural product derived from plants by contacting said first natural product derived from plants with water to form a solution, and thereafter diluting said solution with said one or more polar solvents.

* * * * *

UNITED STATES PATENT AND TRADEMARK OFFICE
CERTIFICATE OF CORRECTION

PATENT NO.   : 6,485,756 B1
DATED        : November 26, 2002
INVENTOR(S)  : Duncan T. Aust et al.

It is certified that error appears in the above-identified patent and that said Letters Patent is hereby corrected as shown below:

Title page,
Item [73], Assignee, delete "Collaborative Technologies, Inc." and substitute
-- Collaborative Laboratories, Inc. --

Signed and Sealed this

First Day of July, 2003

JAMES E. ROGAN
*Director of the United States Patent and Trademark Office*